(12) United States Patent
Brown et al.

(10) Patent No.: US 6,945,056 B2
(45) Date of Patent: Sep. 20, 2005

(54) SYSTEMS AND METHODS FOR FREEZING, MIXING AND THAWING BIOPHARMACEUTICAL MATERIAL

(75) Inventors: David C. Brown, Chicago, IL (US); Jonathan Cutting, Fairfield, CA (US); Eric K. Lee, Acton, MA (US); Nicolas Voute, Cuges les Pins (FR); Brian J. Woodard, Chicago, IL (US)

(73) Assignee: Integrated Biosystems, Inc., Napa, CA (US)

(*) Notice: Subject to any disclaimer, the term of this patent is extended or adjusted under 35 U.S.C. 154(b) by 38 days.

(21) Appl. No.: 10/455,222

(22) Filed: Jun. 4, 2003

(65) Prior Publication Data

US 2004/0006999 A1 Jan. 15, 2004

Related U.S. Application Data

(63) Continuation-in-part of application No. 10/254,036, filed on Sep. 23, 2002, now Pat. No. 6,698,213, and a continuation-in-part of application No. 10/254,025, filed on Sep. 23, 2002, now Pat. No. 6,684,646.
(60) Provisional application No. 60/334,622, filed on Nov. 1, 2001.

(51) Int. Cl.[7] .............................................. F25C 1/00
(52) U.S. Cl. ............................................ 62/66; 62/356
(58) Field of Search ........................... 62/66, 340, 356; 249/112, 121, 127, 130

(56) References Cited

U.S. PATENT DOCUMENTS

| | | | |
|---|---|---|---|
| 2,662,520 A | 12/1953 | McMahon | 128/1 |
| 2,775,101 A | 12/1956 | Hanson | 62/108 |
| 2,964,920 A | 12/1960 | Staebler | 62/60 |
| 2,966,041 A | 12/1960 | Zearfoss, Jr. et al. | 62/60 |
| 3,121,627 A | 2/1964 | Harris | 62/58 |
| 3,389,974 A | 6/1968 | Barattini et al. | 23/295 |
| 3,940,232 A | 2/1976 | Stock | 425/447 |
| 3,952,536 A | 4/1976 | Faust et al. | 62/293 |
| 3,959,981 A | 6/1976 | Anderson | 62/135 |
| 4,018,911 A | 4/1977 | Lionetti et al. | 424/101 |
| 4,030,314 A | 6/1977 | Strehler et al. | 62/65 |
| 4,090,374 A | 5/1978 | Faust et al. | 62/341 |

(Continued)

FOREIGN PATENT DOCUMENTS

| | | | |
|---|---|---|---|
| DE | 3047784 A1 | 7/1982 | C12N/5/00 |
| DE | 3833753 A1 | 8/1989 | F25D/3/10 |

(Continued)

OTHER PUBLICATIONS

Stahl, A.L., "Concentration of Citrus Juices by Freezing", Florida State Horticultural Society, 1944, pp. 43–45.

(Continued)

*Primary Examiner*—William E. Tapolcai
(74) *Attorney, Agent, or Firm*—Heslin Rothenberg Farley & Mesiti P.C.; Nicholas Mesiti, Esq.; Victor A. Cardona, Esq.

(57) ABSTRACT

A system for controlled freezing, storing and thawing of a biopharmaceutical material includes a cavity for receiving a container for holding the biopharmaceutical material. Further included are at least a pair of opposed surfaces facing the biopharmaceutical material holding container. At least one of the opposed surfaces includes a moveable contacting surface configured to contact the container to inhibit a clearance between the container and the movable contacting surface. Also included is at least one heat transfer surface which is thermally coupled to the biopharmaceutical material holding container when the moveable contacting surface contacts the container. Also, the cavity may be configured to receive a frame for supporting the container holding the biopharmaceutical material. Further, the system may include a driver to move the frame holding the container inside the cavity.

28 Claims, 13 Drawing Sheets

U.S. PATENT DOCUMENTS

| | | | |
|---|---|---|---|
| 4,107,937 A | 8/1978 | Chmiel | 62/64 |
| 4,178,776 A | 12/1979 | Baldus et al. | 62/538 |
| 4,194,369 A | 3/1980 | Faust et al. | 62/371 |
| 4,251,995 A | 2/1981 | Pert et al. | 62/60 |
| 4,304,293 A | 12/1981 | Scheiwe et al. | 165/12 |
| 4,327,799 A | 5/1982 | Scheiwe et al. | 165/2 |
| 4,336,435 A | 6/1982 | Kashyap et al. | 219/10.55 |
| 4,469,227 A | 9/1984 | Faust | 206/527 |
| 4,473,739 A | 9/1984 | Scheiwe et al. | 219/302 |
| 4,486,389 A | 12/1984 | Darnell et al. | 422/307 |
| 4,490,982 A | 1/1985 | Christmas | 62/3 |
| 4,531,373 A | 7/1985 | Rubinsky | 62/63 |
| 4,565,073 A | 1/1986 | Lavender | 62/373 |
| 4,580,409 A | 4/1986 | Angelier et al. | 62/340 |
| 4,584,843 A | 4/1986 | Pronger, Jr. et al. | 62/123 |
| 4,587,810 A | 5/1986 | Fletcher | 62/3 |
| 4,596,120 A | 6/1986 | Knodel et al. | 62/59 |
| 4,609,036 A | 9/1986 | Schrader | 165/10 |
| 4,652,712 A | 3/1987 | Zeipel | 219/10.55 |
| 4,669,271 A | 6/1987 | Noel | 62/60 |
| 4,712,607 A | 12/1987 | Lindeman et al. | 165/30 |
| 4,793,151 A | 12/1988 | Masel et al. | 62/306 |
| 4,799,358 A | 1/1989 | Knopf et al. | 62/3 |
| 4,801,777 A | 1/1989 | Auerbach | 219/10.55 |
| 4,843,827 A | 7/1989 | Peppers | 62/73 |
| 4,874,915 A | 10/1989 | Harms et al. | 219/10.55 |
| 4,893,670 A | 1/1990 | Joshi et al. | 165/40 |
| 4,954,679 A | 9/1990 | Harms et al. | 219/10.55 |
| 4,967,564 A | 11/1990 | Strasser | 62/47.1 |
| 4,971,737 A | 11/1990 | Infanti | 264/28 |
| 4,976,308 A | 12/1990 | Faghri | 165/10 |
| 4,986,080 A | 1/1991 | Grigoli et al. | 62/75 |
| 5,005,371 A | 4/1991 | Yonezawa et al. | 62/238.6 |
| 5,022,149 A | 6/1991 | Abbott | 29/890.048 |
| 5,022,236 A | 6/1991 | Knippscheer et al. | 62/529 |
| 5,029,634 A | 7/1991 | Hurner | 165/47 |
| 5,033,544 A | 7/1991 | Abbott | 165/184 |
| 5,054,548 A | 10/1991 | Zohler | 165/133 |
| 5,072,569 A | 12/1991 | VanTassel | 52/745 |
| 5,090,207 A | 2/1992 | Gilbertson et al. | 62/59 |
| 5,103,651 A | 4/1992 | Coelho et al. | 62/341 |
| 5,125,900 A | 6/1992 | Teves | 604/114 |
| 5,168,725 A | 12/1992 | Margolin | 62/457.9 |
| 5,176,197 A | 1/1993 | Hamaguchi et al. | 164/459 |
| 5,181,387 A | 1/1993 | Meckler | 62/59 |
| 5,205,128 A | 4/1993 | Richard | 62/63 |
| 5,212,957 A | 5/1993 | Ruff | 62/124 |
| 5,220,954 A | 6/1993 | Longardner et al. | 165/10 |
| 5,243,833 A | 9/1993 | Coelho et al. | 62/376 |
| 5,285,657 A | 2/1994 | Bacchi et al. | 62/457.9 |
| 5,332,034 A | 7/1994 | Chiang et al. | 165/184 |
| 5,374,436 A | 12/1994 | White et al. | 426/249 |
| 5,411,078 A | 5/1995 | Ares | 165/113 |
| 5,458,191 A | 10/1995 | Chiang et al. | 165/133 |
| 5,476,763 A | 12/1995 | Bacchi et al. | 435/284.1 |
| 5,520,885 A | 5/1996 | Coelho et al. | 422/101 |
| 5,524,706 A | 6/1996 | Nakamura et al. | 165/47 |
| 5,535,598 A | 7/1996 | Cothern et al. | 62/356 |
| 5,557,943 A | 9/1996 | Coelho et al. | 62/376 |
| 5,579,830 A | 12/1996 | Giammaruti | 165/104.27 |
| 5,582,856 A | 12/1996 | White et al. | 426/249 |
| 5,609,035 A | 3/1997 | Cothern et al. | 62/73 |
| 5,616,268 A | 4/1997 | Carr | 219/687 |
| 5,638,686 A | 6/1997 | Coelho et al. | 62/51.1 |
| 5,644,922 A | 7/1997 | Linden et al. | 62/51.1 |
| 5,689,961 A | 11/1997 | Cosman | 62/78 |
| 5,750,658 A | 5/1998 | Coelho et al. | 530/382 |
| 5,779,974 A | 7/1998 | Kuzyk | 422/44 |
| 5,862,675 A | 1/1999 | Scaringe et al. | 62/193.3 |
| 5,863,715 A | 1/1999 | Rajotte et al. | 435/1.3 |
| 5,873,254 A | 2/1999 | Arav | 62/63 |
| 5,884,490 A | 3/1999 | Whidden | 62/70 |
| 5,939,023 A | 8/1999 | Coelho et al. | 422/101 |
| 5,964,095 A | 10/1999 | Coelho et al. | 62/62 |
| 5,964,100 A | 10/1999 | Wisniewski | 62/373 |
| 5,988,422 A | 11/1999 | Vallot | 220/62.22 |
| 5,996,427 A | 12/1999 | Masek et al. | 73/864.91 |
| 5,999,701 A | 12/1999 | Schmidt | 392/470 |
| 6,007,773 A | 12/1999 | Kuzyk | 422/44 |
| 6,065,294 A | 5/2000 | Hammerstedt et al. | 62/3.3 |
| 6,077,447 A | 6/2000 | Coelho et al. | 210/774 |
| 6,079,215 A | 6/2000 | Wisniewski | 62/46.1 |
| 6,098,410 A | 8/2000 | Horigane | 62/62 |
| 6,123,696 A | 9/2000 | Coelho et al. | 604/410 |
| 6,146,124 A | 11/2000 | Coelho et al. | 425/387.1 |
| 6,196,296 B1 | 3/2001 | Wisniewski et al. | 165/47 |
| 6,220,038 B1 | 4/2001 | Marsh et al. | 62/71 |
| 6,232,115 B1 | 5/2001 | Coelho et al. | 435/307.1 |
| 6,274,090 B1 | 8/2001 | Coelho et al. | 422/101 |
| 6,302,327 B1 | 10/2001 | Coelho et al. | 235/383 |
| 6,371,121 B1 | 4/2002 | Faries, Jr. et al. | 128/849 |
| 6,384,380 B1 | 5/2002 | Faries, Jr. et al. | 219/385 |
| 6,387,322 B1 | 5/2002 | Gallus | 422/38 |
| 6,393,860 B1 | 5/2002 | Heschel et al. | 62/376 |
| 6,453,683 B1 | 9/2002 | Wisniewski et al. | 62/75 |

FOREIGN PATENT DOCUMENTS

| | | | |
|---|---|---|---|
| DE | 4029216 | 3/1992 | |
| EP | 0726080 A2 | 12/1995 | |
| EP | 1 134 000 A2 | 9/2001 | |
| FR | 758510 | 1/1934 | |
| FR | 2501057 | 10/1981 | B01F/11/00 |
| GB | 2 196 830 A | 5/1988 | |
| GB | 2240165 A | 7/1991 | |
| GB | 2351799 A | 1/2001 | |
| WO | EP 0195919 A2 | 2/1986 | A23B/4/06 |
| WO | EP 0647707 A2 | 7/1994 | C12M/1/00 |
| WO | WO 97/18424 | 5/1997 | |
| WO | WO 97/24152 | 7/1997 | A61M/1/36 |
| WO | WO 98/23907 | 6/1998 | |
| WO | WO 98/34078 | 8/1998 | |
| WO | WO 00/72902 | 12/2000 | A61M/5/44 |

OTHER PUBLICATIONS

Kalhori, B. et al., "Studies on Heat Transfer From a Vertical Cylinder, With or Without Fins, Embedded in a Solid Phse Change Mediam", Transactions of the ASME, Journal of Heat Transfer, vol. 107, Feb. 1985, pp. 44–51.

Wisniewski, et al., "Large–Scale Freezing and Thawing of Biopharmaceutical Drug Product", Proceedings of the International Congress: Advanced Technologies For Manufacturing Of Aseptic & Terminally Sterilized Pharmaceuticals & Biopharmaceuticals, Basel, Switzerland, Feb. 17–19, 1992, pp. 132–140.

Wisniewski et al., Large–Scale Freezing and Thawing of Biopharmaceutical Drug Product, PharmTech Conference, Sep. 16–19, 1996, Sheraton Meadowlands, East Rutherford, New Jersey.

Wisniewski et al., "Large–Scale Freezing and Thawing of Biopharmaceutical Products", Biotechnology and Biopharmaceutical Manufacturing, Processing and Preservation, pp. 7–59.

Wisniewski, Richard, "Developing Large–Scale Cryopreservation Systems for Biopharmaceutical Products", BioPharm, Jun. 1998, pp. 50–60.

Wu, et al., "Scale–Down Approach to Large Volume Cryopreservation of Biopharmaceuticals Using the CryoCassette™ and CyroWedge™ ", Integrated Biosystems, 2000, 4 pages.

L. Quan et al., "Effects of Vibration on Ice Contact Melting Within Rectangular Enclosures", Transactions of the ASME 120:518–520 (May 1998).

Burton et al., "An Experimental Investigation of the Solidification Process in a V-Shaped Sump", Inter. J. Heat Mass Transfer, vol. 18, pp. 2383–2393, 1995.

Avis et al., *Cryopreservation Applications in Pharmaceuticals and Biotechnology*, Drug Manufacturing Technology Series 5, "Large–Scale Cryopreservation: Process Development for Freezing and Thawing of Large Volumes of Cell Suspensions, Protein Solutions, and Biological Products", Wisniewski, pp. 181–197.

Wisniewski, Bioprocessing Controlled Freeze/Thaw for Biopharmaceuticals, Tutorial: Preservation of Bioproducts Using Controlled Freeze/Thaw Operations, Genetic Engineering News, Feb. 15, 2003, vol. 32, No. 4, pp. 36 & 38.

Double Contact PlateFreezers, Dole Plate Freezers, www.b-mil.com/dole, copyright 1996, BMIL International.

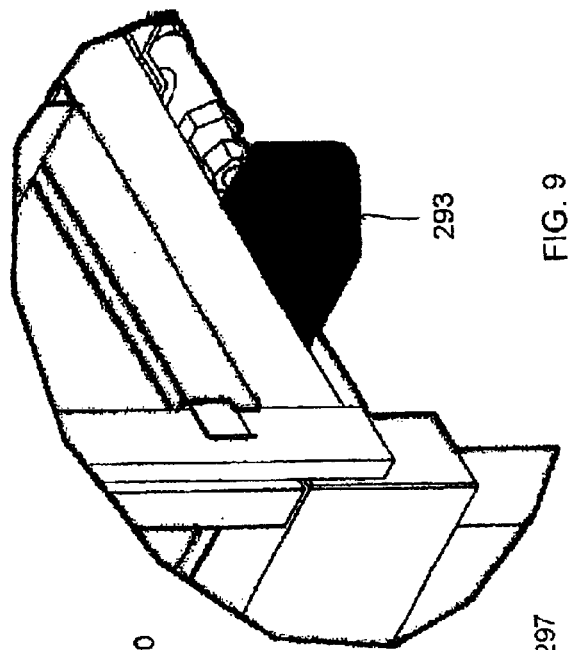
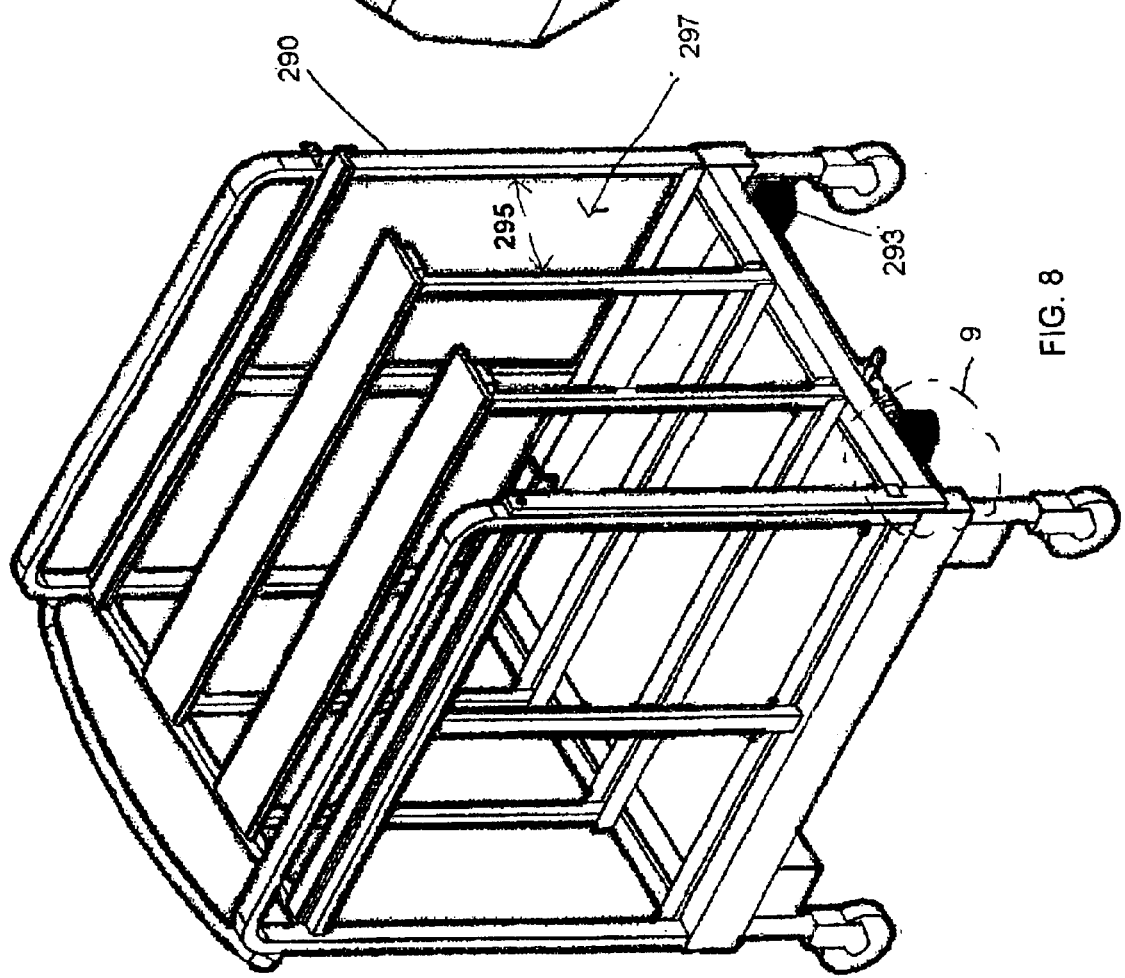

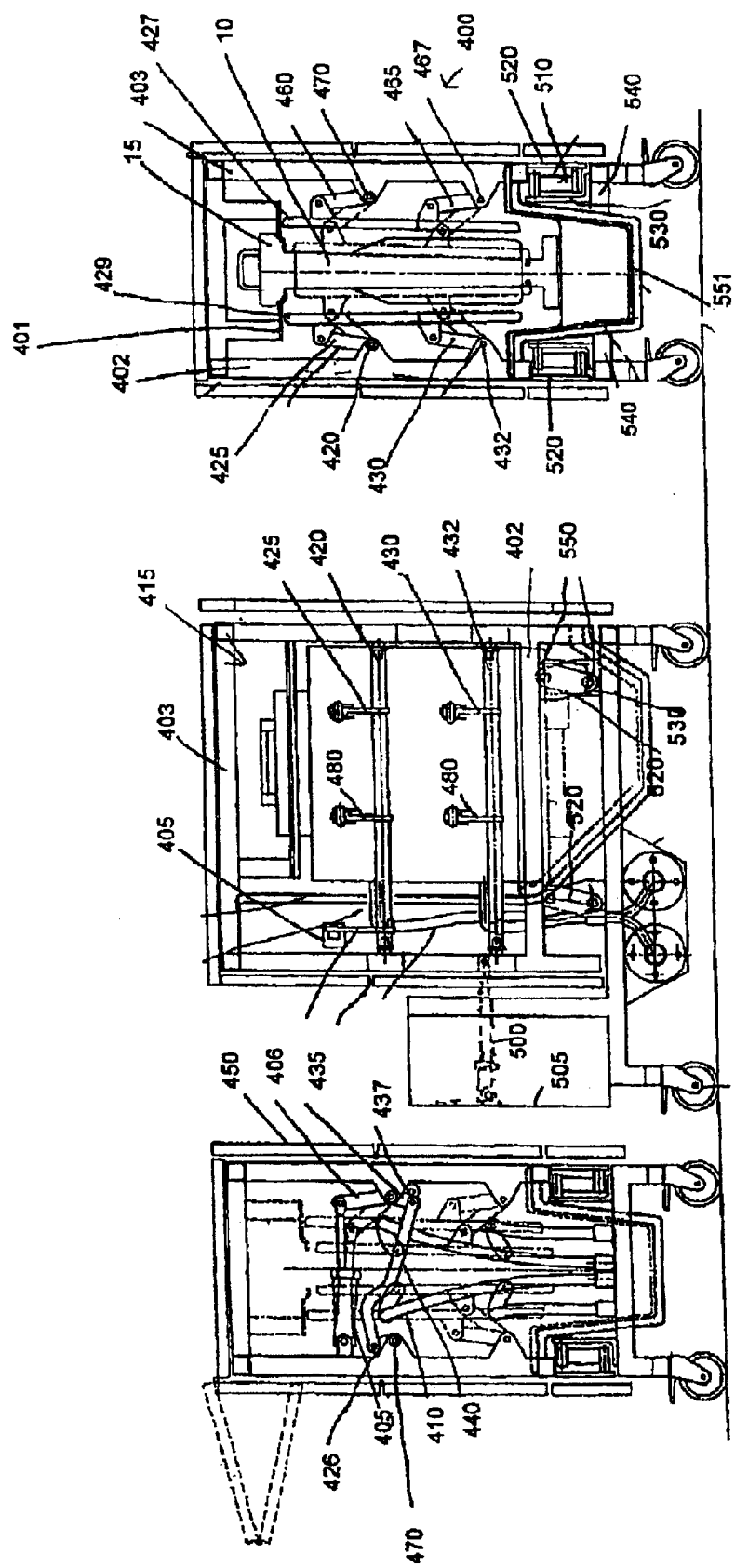

SYSTEMS AND METHODS FOR FREEZING, MIXING AND THAWING BIOPHARMACEUTICAL MATERIAL

CROSS-REFERENCE TO RELATED APPLICATIONS

This application is a Continuation-In-Part of U.S. application Ser. No. 10/254,036 filed on Sep. 23, 2002, Now U.S. Pat. No. 6,698,213 and titled "Systems and Methods for Freezing, Storing and Thawing Biopharmaceutical Material", which claims the benefit of U.S. Provisional Application No. 60/334,622, filed Nov. 1, 2001, both of which are incorporated herein by reference. Also this application is a Continuation-In-Part of U.S. application Ser. No. 10/254,025 filed on Sep. 23, 2002, Now U.S. Pat. No. 6,684,646 and titled "Systems and Methods for Freezing, Storing, and Thawing Biopharmaceutical Material", which claims the benefit of U.S. Provisional Application No. 60/334,622, filed Nov. 1, 2001, both of which are incorporated herein by reference. Further, the contents of U.S. patent application Ser. No. 10/455,223, and titled "Systems And Methods For Freezing, Storing, Transporting And Thawing Biopharmaceutical Material", filed on Jun. 4, 2003, is incorporated herein by reference. Also, the contents of U.S. application Ser. No. 09/905,488 filed on Jul. 13, 2001 (U.S. Pat. No. 6,453,683 B1 granted on Sep. 24, 2002) and U.S. application Ser. No. 09/863,126, filed on May 22, 2001 are incorporated herein by reference.

TECHNICAL FIELD

This invention relates, in general, to biopharmaceutical materials, preservation methods and systems, and more particularly to systems and methods for freezing, mixing, and thawing of biopharmaceutical materials.

BACKGROUND ART

Preservation of biopharmaceutical materials, such as cryopreservation, is important in the manufacture, use, transport, storage and sale of such materials. For example, biopharmaceutical materials are often preserved by freezing between processing steps and during storage. Similarly, biopharmaceutical materials are often frozen and thawed as part of the development process to enhance the quality or to simplify the development process.

When freezing biopharmaceutical materials, the overall quality, and in particular pharmaceutical activity, of the biopharmaceutical materials is desirably preserved, without substantial degradation of the biopharmaceutical materials.

Currently, preservation of biopharmaceutical material, particularly in bulk quantities, often involves placing a container containing liquid biopharmaceutical material in a cabinet freezer, chest freezer or walk-in freezer and allowing the biopharmaceutical material to freeze. Specifically, the container, which is typically one or more liters in volume and may range up to ten or more liters, is often placed on a shelf in the cabinet freezer, chest freezer or walk-in freezer and the biopharmaceutical material is allowed to freeze. These containers may be stainless-steel vessels, plastic bottles or carboys, or plastic bags. They are typically filled with a specified volume to allow for freezing and expansion and then transferred into the freezers at temperatures typically ranging from negative 20 degrees Celsius to negative 70 degrees Celsius or below.

To ensure efficient use of available space inside the freezer, containers are placed alongside one another and sometimes are stacked into an array with varied spatial regularity. Under these conditions, cooling of the biopharmaceutical solution occurs at different rates depending on the exposure of each container to the surrounding cold air, and the extent to which that container is shielded by neighboring containers. For example, containers placed close to the cooling source or those on the outside of an array of containers would be cooled more rapidly than those further away from the cooling source and/or situated at the interior of the array.

In general, adjacent placement of multiple containers in a freezer creates thermal gradients from container to container. The freezing rate and product quality then depend on the actual freezer load, space between the containers, and air movement in the freezer. This results in a different thermal history for the contents of the containers depending on their location in a freezer, for example. Also, the use of different containers for individual portions of a single batch of biopharmaceutical material may cause different results for portions of the same batch due to different thermal histories resulting from freezing in a multiple container freezer, particularly if the storage arrangement is haphazard and random. Another consequence of obtaining a range of freezing times is that certain containers may freeze so slowly that the target solute can no longer be captured within the ice phase, but remains in a progressively smaller liquid phase. This phenomenon is referred to as cyroconcentration. In some cases such cyroconcentration could result in precipitation of the biopharmaceutical product, thus resulting in product loss.

Disposable bulk storage containers such as plastic bags or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic bags, during freezing, thawing, or transportation of these containers often result in damage thereof, due, for example, to shock, abrasion, impact, or other mishandling events arising from operator errors or inadequate protection of the bags in use.

Similarly, thawing of bulk biopharmaceutical materials typically involved removing them from a freezer and allowing them to thaw at room temperature. Such uncontrolled thawing can also lead to product loss. Generally, rapid thawing of biopharmaceutical materials results in less product loss than slower thawing. Further, it may also be desirable to control temperature of the biopharmaceutical materials during a thawing process since exposure of some biopharmaceutical materials to elevated temperatures may also lead to product loss. For example, it may be desirable to maintain a thawing biopharmaceutical material at about 0° C. when still in liquid and solid form during thawing thereof.

Further, it may be desirable to mix liquid bulk biopharmaceutical material at a homogeneous temperature above, below, or at an ambient temperature level. The mixing of biopharmaceutical materials in containers is important in the manufacture, use, transport, and storage of such materials. For example, biopharmaceutical materials are often blended, compounded, or formulated by mixing during processing steps and kept homogeneous during storage. Similarly, biopharmaceutical materials are often blended, compounded, or formulated by mixing as part of this development process to enhance the quality or to simplify the development process.

Currently, in some aspects, mixing of bulk biopharmaceutical materials involves transferring the product out of a container comprising the biopharmaceutical materials into a tank with a mechanical agitator, mixing and transferring the material back to the container. During those operations the containment may be broken and the product sterility and purity compromised. The homogeneous product may separate again after transfer back to its original container. Multiple transfers may expose product to excessive shear and to gas-liquid interfaces, which may adversely affect the product. Thus, it is preferable if such mixing can be accomplished without transferring the biopharmaceutical material out of the container or inserting a mixer into the container, i.e., noninvasive mixing is preferred. When utilizing such noninvasive mixing, the overall quality, sterility, and in particular pharmaceutical activity, of the biopharmaceutical materials is desirably preserved, without substantial degradation of the biopharmaceutical materials.

Thus, there is a need for systems and methods for freezing, thawing and mixing biopharmaceutical materials, particularly in bulk quantities, that are controlled, do not result in loss of biopharmaceutical material, and are repeatable.

SUMMARY OF THE INVENTION

The present invention provides, in a first aspect, a system for freezing a biopharmaceutical material, particularly in bulk quantities, which includes a cavity for receiving a container for holding the biopharmaceutical material. The system further includes at least a pair of opposed surfaces facing the biopharmaceutical material holding container. At least one of the opposed surfaces includes a moveable contacting surface configured to contact the container to inhibit a clearance between the container and the contacting surface. Also included is at least one heat transfer surface which is thermally coupled to the biopharmaceutical material holding container when the moveable contacting surface contacts the container.

The present invention provides, in a second aspect, a method for freezing a biopharmaceutical material, particularly in bulk quantities. The method includes inserting a container for holding the biopharmaceutical material into a cavity of a temperature control unit. The method further includes moving at least one contacting surface in the cavity to contact the container with at least one heat transfer surface to inhibit a clearance between the container and the at least one heat transfer surface.

The present invention provides, in a third aspect, a system for freezing, thawing, or mixing a biopharmaceutical material, particularly in bulk quantities, which includes a cavity for receiving a container for holding the biopharmaceutical material. Further included is a driver for moving the container in the cavity and means for controlling the temperature of the cavity to control the temperature of the biopharmaceutical material.

The present invention provides, in a fourth aspect, a method for freezing, thawing, or mixing a biopharmaceutical material which includes inserting a biopharmaceutical material holding container into a cavity of a temperature control unit. Also, a temperature of the cavity is controlled and the container is operatively moved within the temperature control unit.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

FIG. 8 is another example of a transportation cart having aligning tabs;

FIG. 9 is an enlarged perspective view of the aligning tabs on the transportation cart on FIG. 8;

FIG. 10 is a left side cross-sectional view of another embodiment of a temperature control unit in accordance with the present invention;

FIG. 11 is a front cross-sectional view of the system of FIG. 10 with a frame received therein;

FIG. 12 is a right side cross-sectional view of the temperature control unit of FIG. 10;

DETAILED DESCRIPTION

In accordance with the principles of the present invention, systems and methods for freezing, thawing, and/or mixing biopharmaceutical materials are provided.

In an exemplary embodiment depicted in FIGS. 1–7, portions of a system for cooling, freezing, preserving, processing, thawing, and/or mixing biopharmaceutical materials are shown. The system may include a temperature control unit 20 (e.g., a freeze-thaw module) configured to receive a sterile container, such as a flexible container 10 adapted to contain the biopharmaceutical materials. Further, temperature control unit 20 may be configured to receive a supporting structure, such as a frame 15, for supporting container 10.

Figure 1:
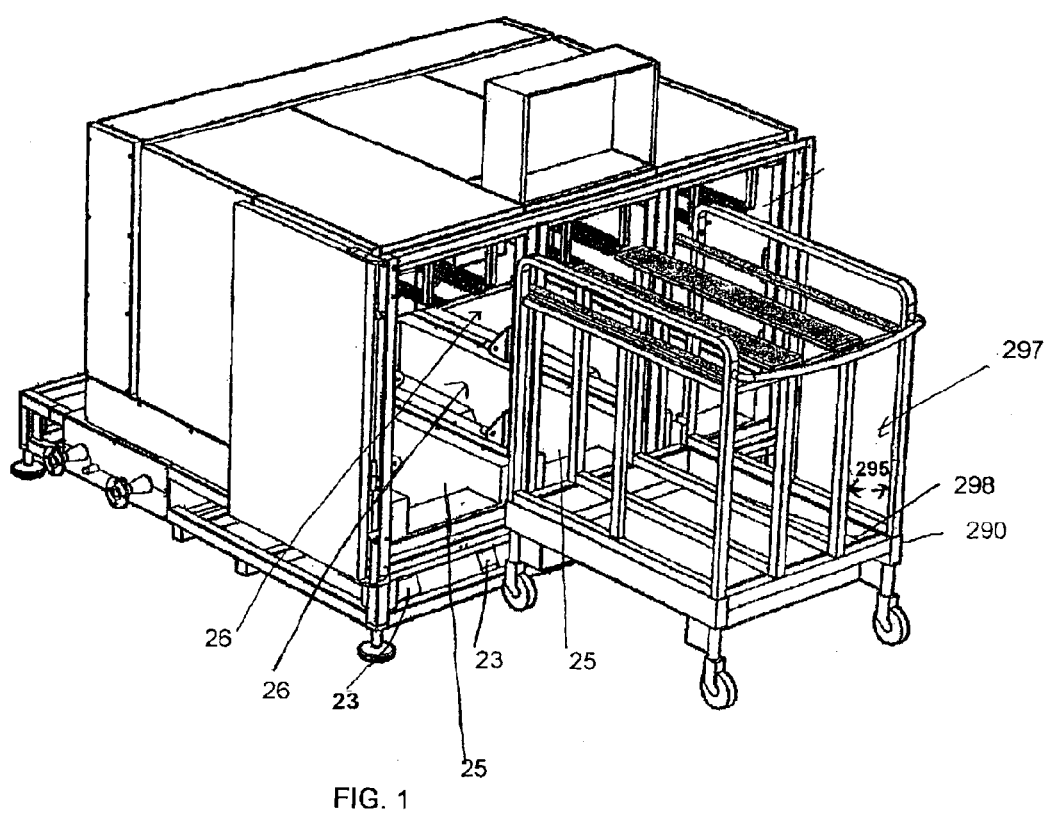
FIG. 1 is a perspective view of a temperature control unit adjacent a transportation cart with the temperature control unit receiving a frame supporting a flexible container, in accordance with the present invention.
Figure 2:
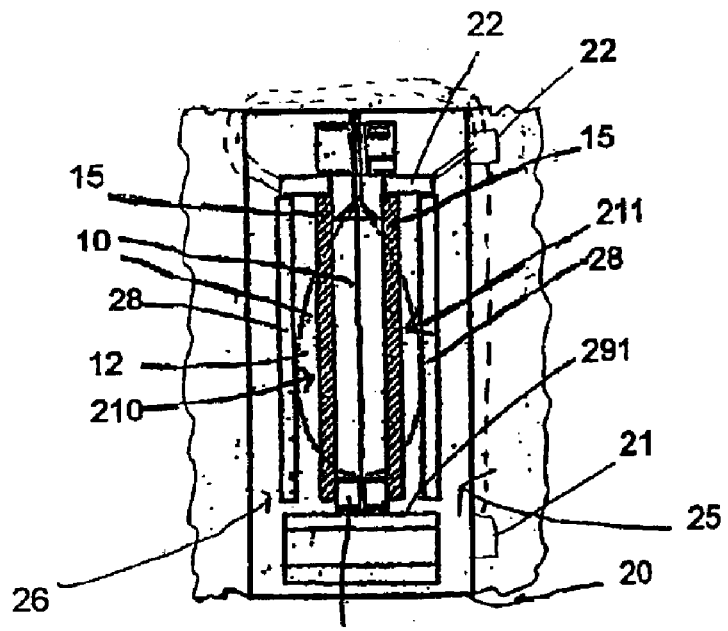
FIG. 2 is a side cross-sectional view of the temperature control unit of FIG. 1.
Figure 3:
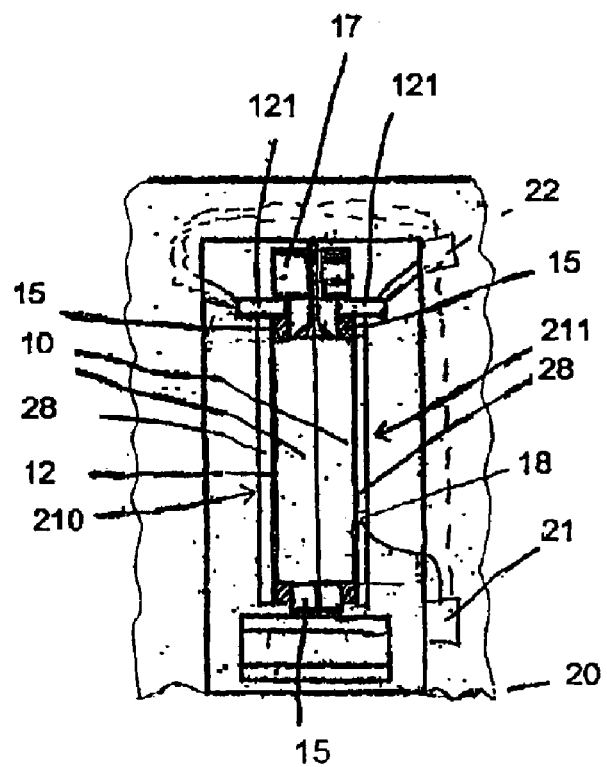
FIG. 3. is a side cross-sectional view of the temperature control unit of FIG. 1 shown with plates compressing the flexible container.

Temperature control unit 20 is configured to control the temperature of a cavity or an interior 26 thereof, which may include one or more slots 25 as depicted in FIGS. 1–3. Also, temperature control unit 20 may include therein, or may be coupled to, a controller portion 21 and/or a sensor (e.g. a temperature sensor 18) to allow a user to control the heating, cooling, freezing, agitating, thawing, or mixing, for example, of the biopharmaceutical materials in flexible container 10, when it is inserted into interior 26 of temperature control unit 20. Heating, cooling, freezing or thawing of the contents of flexible containers 10 placed inside temperature control unit 20 may be controlled by blowing a continuous stream of cold or warm air, by direct contact of the containers with cold or warm surfaces, or by spraying cooling fluid thereon (e.g., liquid nitrogen), for example.

In one embodiment, temperature control unit 20 includes a heat exchanger having one or more heat transfer or conduction plates for heating and/or cooling flexible container 10 and biopharmaceutical materials contained therein, as best depicted in FIG. 2 which illustrates a front cross-sectional view of one of slots 25 of interior 26. For example, temperature control unit 20 may include heat transfer plates 28 for contacting flexible container 10 to cool or heat the contents thereof. One or more of plates 28 could have heat transfer fluids circulating therethrough, such as water, oil, glycol, silicone fluid, hot air, cold air, alcohol, freons, freezing salty brines, liquid nitrogen or other heat transfer fluids as is known by those skilled in the art. Plates 28 could further include heat transfer enhancing structures such as fins and pins due to required high heat flux for product thawing, as will be understood by those skilled in the art.

One or more plates 28 may also include temperature sensor 18 mounted on an interior portion or exterior portion of plates 28 or it may be integral thereto. Temperature sensor 18 may detect a temperature of one or more of plates 28 and one or more locations thereon. Controller portion 21 of temperature control unit 20 may be coupled to temperature sensor 18 and to a heat transfer fluid control portion 22 of temperature control unit 20. Such heat transfer fluids may be circulated through plates 28 by heat transfer fluid control portion 22 controlled by controller portion 21 in response to temperatures detected by temperature sensor 18. Controller portion 21 may control heat transfer control portion 22 to control a temperature of the heat transfer fluid.

In another example, a temperature sensor (not shown) could be located in a heat transfer fluid input (not shown) of a plate and/or a heat transfer output (not shown) of such a plate. A difference between the temperatures determined at such points could be utilized to determine the temperature of the biopharmaceutical materials held in container 10. Thus, controller 21 may regulate a flow of heat transfer fluid to one or more of plates 28 to regulate a temperature of the biopharmaceutical materials held in container 10 in slot 25 of interior 26 of temperature control unit 20. More specifically, controller 21 may cause a heat transfer fluid control portion 22 to circulate heat transfer fluids in plate(s) 28 to raise or lower a temperature of plate(s) 28, thereby lowering or raising the temperature of container 10 which is in contact with plate 28. In this manner, the biopharmaceutical material may have its temperature controlled (i.e., it may be thawed or frozen). Alternatively, such control of heat transfer plates 28 may be performed by controller portion 21 controlling flow of heat transfer fluid to plates 28 in a predetermined manner without feedback from a sensor coupled to plates 28 or the heat transfer fluid.

Further examples of temperature sensors and control of biopharmaceutical materials held in temperature control units are fully described in co-owned U.S. application Ser. No. 10/188,639 filed Jul. 15, 2002 and entitled Cryopreservation System with Controlled Dendritic Freezing Front Velocity which is a continuation-in-part of U.S. Pat. No. 6,453,683 which is a continuation-in-part of U.S. patent application Ser. No. 09/863,126, the entireties of which are incorporated herein by reference.

Also, one or more of plates 28 may be moveable to allow compression of flexible container 10, when flexible container 10 is received in frame 15 and frame 15 is received in slot 25 of interior 26 of temperature control unit 20, as depicted in FIGS. 2–3. Further, plates 28 could be stationary and temperature control unit 20 may include one or more non-temperature controlled moveable plates, surfaces, or walls (not shown) configured to compress flexible container 10, when flexible container 10 and frame 15 are received in slot 25. In one example, such non-temperature controlled movable plates may compress a container while the container is cooled by blast freezing, or other means of controlling a temperature of the container without contacting heat transfer plates therewith, e.g., via convective cooling. Alternatively, plates 28 may control the temperature of the container and may be movable along with such additional non-temperature controlled movable plates, surfaces, or walls.

Flexible container 10 may be formed of a laminated film which includes a plurality of layers and may have an interior volume ranging from 0.01–100 liters, for example. Further, flexible container 10 could be available in a variety of sizes to accommodate different uses, for example, 8.3 and 16.6 liter flexible containers may be utilized. Also a biocompatible product-contacting layer of the interior of flexible container 10 may be formed of a low density polyethylene, very low density polyethylene ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with warm and cold conditions and may be able to withstand ionizing irradiation for sterilization purposes. Also, flexible container 10 may have a large surface area to volume ratio, and a relatively thin wall thus promoting heat transfer therethrough when received in temperature control unit 20. One example of materials useful for formulation of flexible container 10 is described in U.S. Pat. No. 5,988,422 to Vallot, the entire subject matter of which is hereby incorporated herein by reference. Also, flexible container 10 may be disposable, thus promoting ease of use and preventing cross-contamination of the interior of flexible container 10 which might result when reusing other types of containers.

Container 10 may be configured to receive and contain frozen and/or liquid biopharmaceutical materials. In an embodiment, the biopharmaceutical materials may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, antibodies and their fragments, enzymes and their fragments, vaccines, viruses and their fragments, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, mixtures of the above and biocatalysts and their fragments.

Figure 5:
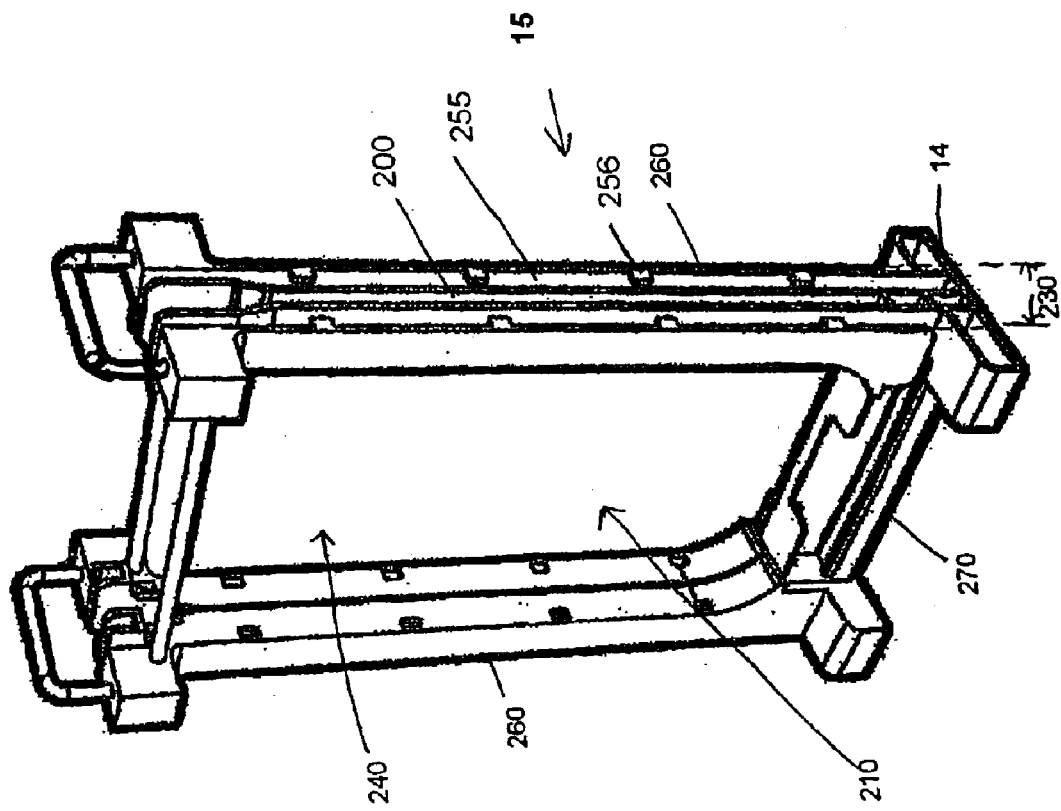
FIG. 5 is a perspective view of a frame for use with the flexible container of FIG. 4 and temperature control unit of FIG. 1.
Figure 4:
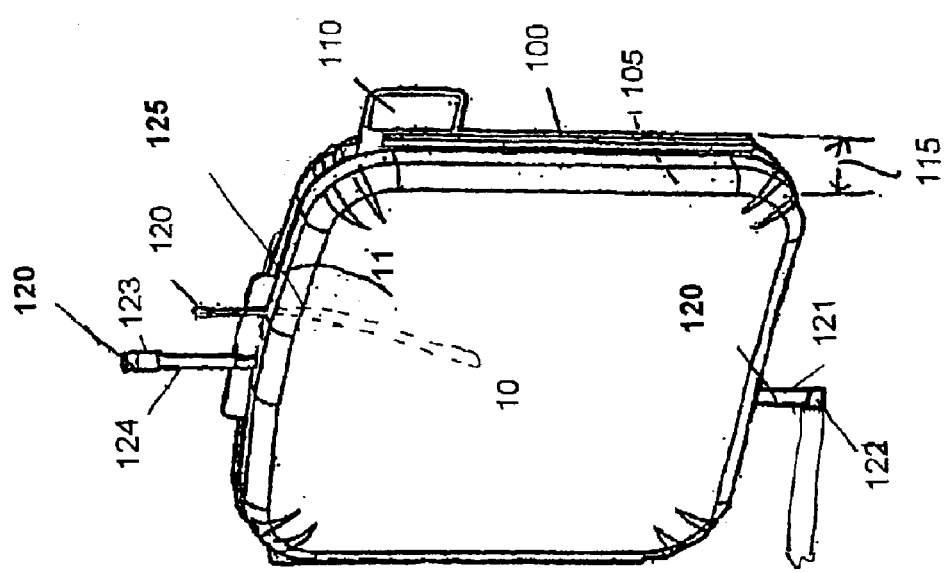
FIG. 4 is a perspective view of a flexible container receivable in the frame and temperature control unit of FIG. 1.
Figure 6:
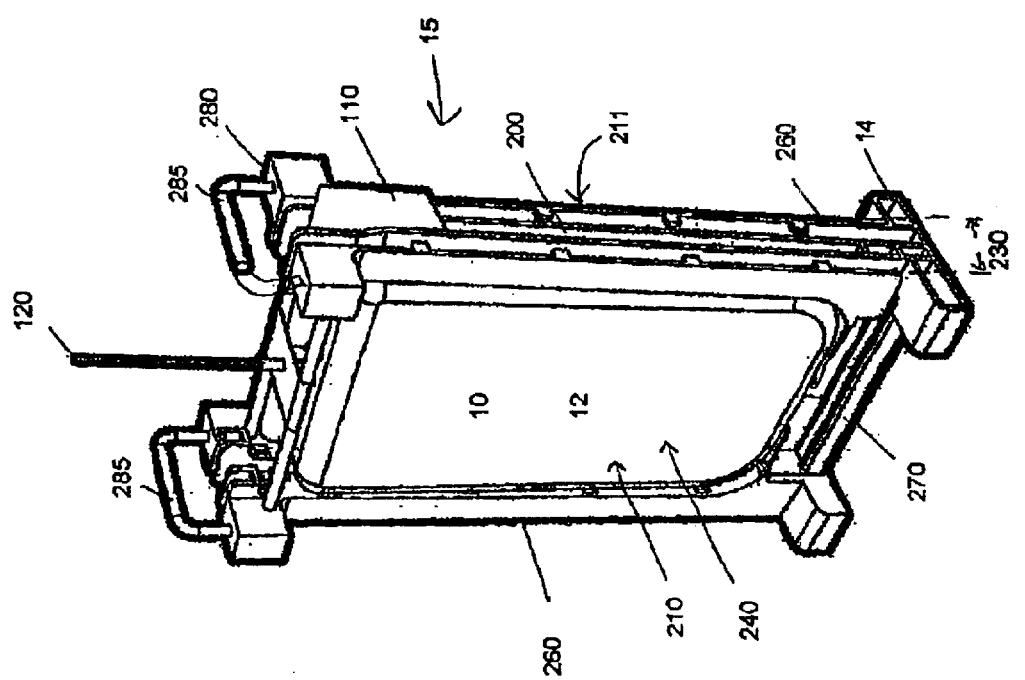
FIG. 6 is a perspective view of the flexible container of FIG. 4 received in the frame of FIG. 5.
Figure 13:
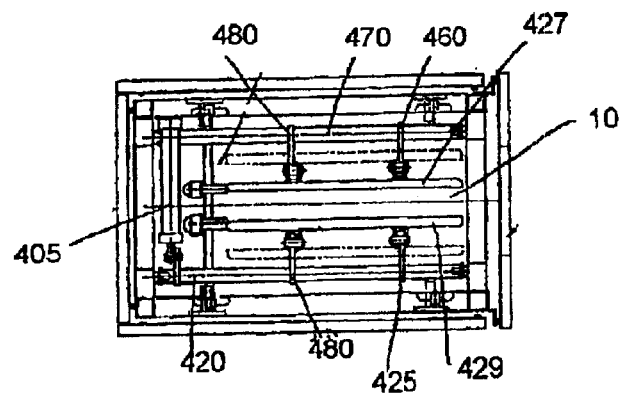
FIG. 13 is a top cross-sectional view of the temperature control unit of FIG. 10.

Sterile, flexible container 10 may be configured to be received in frame 15 for supporting flexible container 10. For example, flexible container 10 may include an outwardly-extending flange 100 adapted to be received in a channel 200 of frame 15, as depicted in FIGS. 4–6. For example, flange 100 could be a plastic reinforcement rod dimensioned to be received in channel 200. Thus, flange 100, and therefore flexible container 10, may be inserted vertically downward or removed vertically upward, but may not be moved laterally or in directions other than up and down due to the engagement of flange 100 with channel 200. Thus, flange 100 serves to support the flexible container 10 laterally, retain a shape of flexible container 10 during filling thereof, reduce sagging of container 10 and ensure dimensional stability of flexible container 10 by spreading a load placed thereon along three different sides of flexible container 10, i.e., both sides and the bottom thereof.

Further, flexible container 10 may include a horizontally extending flange or rod (not shown) projecting from a top side 11 of flexible container 10. The horizontally extending flange may be configured to be received in channel 200 and may be substantially perpendicular to flange 100. The horizontally extending flange also may be configured to connect to a top portion of frame 15 to reduce sag of flexible container 10 when flexible container 10 is received in frame 15.

Flexible container 10 may also include a display tab 110 or other means for receiving a label to provide an indication to a user as to the contents of flexible container 10. Such a label may include written information, an embedded microchip, a RF transmitter and/or an electronic or magnetic bar code for indication of the contents of flexible container 10 to facilitate identification, tracking, and/or characterization of the contents thereof. The use of the label may thus simplify management of materials stored in flexible container 10, received in frame 15, when it is stored in a large freezer containing other frames and flexible containers which may appear similar thereto.

As shown in FIGS. 4 and 6, flexible container 10 may include one or more ports or conduits 120 to allow filling or draining of biopharmaceutical materials or other solids, liquids, or gases into and/or out of the interior (not shown) of flexible container 10. Conduits 120 may also be used to insert a measurement probe (not shown) inside flexible container 10 (e.g., a pH electrode, a conductivity sensor, temperature probe, an ion selective electrode, a spectophotometric probe, an ultrasound sensor, an optic fiber.) Conduits 120 may be positioned in the top part and/or in the bottom part of flexible container 10. The position of the conduits may facilitate filling and/or drainage of the containers. Conduit 120 may be integral to flexible container 10 or it may be connectable to a receiving port (not shown) thereof. For example, conduit 120 could be connected to a receiving port using a fitting placed within the inlet port. Fittings such as those described in U.S. Pat. No. 6,186,932, may be used for the connection of such conduits. Also, fittings which can maintain the sterility of the contents of the container or flexible container may preferably be used. The fittings may be configured in different shapes, such as straight fittings and/or angled fittings including ninety (90) degree elbows, if desired. In another example, conduit 120 may include a filter (not shown) to filter any impurities or other undesirable materials from the biopharmaceutical material.

For example, one of conduits 120 may be a drainage conduit 121 on a bottom portion of container 10. Drainage conduit 121 may include a clamp 122 or a valve (not shown) to allow the selective drainage of container 10. Drainage conduit 121 may further be formed of any of various lengths to allow efficient drainage of container 10. In one example, drainage conduit 121 may be of a length such that it may be received in a conduit receiving groove 255 of frame 15. More specifically, conduit 121 may be of a length allowing it to be extended from the bottom of container 10 to a side of container 10, to the top of frame 15 in groove 255, and back to a bottom of frame 15 in groove 255. Groove 255 may further include retaining members 256 spaced along its length which conduit 121 may be inserted under. Retaining members 256 may extend a portion of a distance across groove 255 (FIG. 8) such that drainage conduit 121 may be inserted under retaining member 256 and retaining member 256 may inhibit movement of drainage conduit 121 out of groove 255. In another example, one of conduits 120 may include a sleeve 125 extending from an exterior of container 10 into an interior thereof such that a temperature probe or other sensing device may be inserted into such sleeve to allow measurement of biopharmaceutical material held in container 10. One example of such a temperature sensor is a resistance temperature detector. In another example, a first top conduit 124 of conduits 120 may include a clamp 123 or a valve (not shown) to allow selective filling and/or draining of the biopharmaceutical material therethrough in a manner similar to drainage conduit 121 and clamp 122.

Frame 15 may be formed to receive and support flexible container 10 to provide additional rigidity and support to flexible container 10, thus facilitating handling, storage, and/or temperature control thereof. Frame 15 may include a first opening 210 and a second opening 211 (FIGS. 2–3 and 5–6) on an opposite side of frame 15 from opening 210. These openings expose a large surface area of flexible container 10 to interior 26 of temperature control unit 20, when received therein. Through these openings, flexible container 10 may contact heat transfer surfaces such as plates 28 (FIGS. 2–3), air at a controlled temperature, or liquid cooling spray within temperature control unit 20. For example, a first side 12 of flexible container 10 may contact a heat transfer surface (e.g., one of plates 28) of interior 26 of temperature control unit 20 (FIG. 1) through opening 210 to control the temperature of the biopharmaceutical material in flexible container 10. Alternatively, side 12 of flexible container 10 may be exposed to a still or circulating air within the temperature control unit 20. For example, the biopharmaceutical material may be frozen or thawed while in flexible container 10, when flexible container 10 is received in frame 15 and frame 15 is received in temperature control unit 20.

Frame 15 may further include upwardly extending sides 260, a bottom 270 and a top 280 to protect and support flexible container 10. Also, top 280 may include one or more handles 285, as best depicted in FIGS. 5 and 6. Frame 15 may preferably be formed of materials which remain stable and retain their structural properties. Specifically, such materials should retain their load-bearing capacity and exhibit glass transition temperatures no higher than negative 80 degrees Celsius while being resistant to cleaning agents and methods commonly used in biopharmaceutical manufacturing, e.g., sodium hydroxide, sodium hypochloride (e.g., CLOROX), peracetic acid, etc.

For example, sides 260 may be formed of fluoropolymer resin (e.g. TEFLON) and top 280 and bottom 270 may be formed of stainless steel. Also, sides 260, bottom 270 and/or top 280 may be made of any number of other materials including aluminum, polyethylene, polypropylene, polycarbonate, and polysulfone, for example. Further materials may include composite materials such as glass-reinforced plastic, carbon-fiber reinforced resins, or other engineering plastic materials known to offer high strength-to-weight rations and which are serviceable at various temperatures of interest. It will be understood by those skilled in the art that sides 260, bottom 270 and/or top 280 may be monolithic and integrally formed as one piece or suitably connected together. Further, sides 260, bottom 270 and/or top 280 could be formed of a same material (e.g. stainless steel) or they could be formed of different materials and connected together. Frame 15 may also include one or more foot members 14 for maintaining frame 15 in an upright position, as depicted in FIGS. 5 and 6. As will be understood by those skilled in the art, foot members 14 may be integral to or connectable to one or more sides 260 of frame 15.

Also, as described above, plates 28 (FIGS. 2–3) of temperature control unit 20 may be configured to contact and compress flexible container 10, when substantially filled with the biopharmaceutical material, and flexible container 10 and frame 15 are received in slot 25 of interior 26 of temperature control unit 20, as depicted in FIGS. 2–3. Further, as depicted in FIG. 3, the contents of flexible container 10 may be frozen or solidified while plates 28 are compressing it in temperature control unit 20 to cause flexible container 10 to have a dimension or width 115 in a direction between first opening 210 and second opening 211 (FIG. 4) of frame 15, which is less than or equal to a dimension or width 230 of an interior 240 of frame 15 in the same direction as width 115. Thus, flexible container 10 having the biopharmaceutical material frozen therein may be confined within an envelope or thickness defined by frame 15. By compressing flexible container 10 in frame 15, a substantially rectangular cross-sectional profile is created of flexible container 10 having the biopharmaceutical material therein. Such a cross-sectional profile promotes contact between flexible container 10 and heat transfer plates 28 as depicted in FIG. 3. This is particularly true in the corners of flexible container 10, thus allowing freezing to proceed in a uniform manner in a direction normal to plates 28. Further, the compression of flexible container 10 may force the biopharmaceutical material in flexible container 10 to occupy any voids or spaces between plates 28 and flexible container 10. By reducing or minimizing such voids or spaces, contact of plates 28 with flexible container 10 may be more uniform and thus cause more uniform cooling of the biopharmaceutical material contained in flexible container 10. Alternatively, the biopharmaceutical material may be heated or thawed in temperature control unit 20 through such contact with plates 28.

Figure 7:
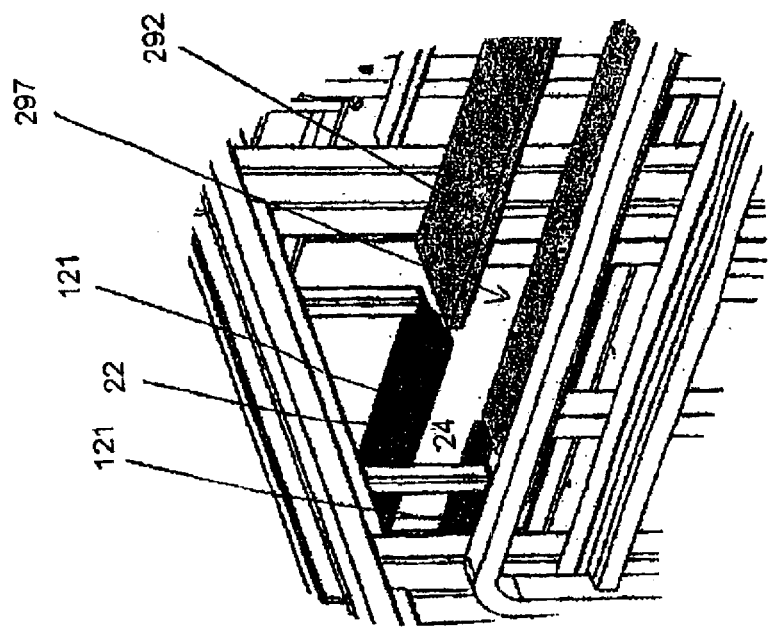
FIG. 7 is a perspective view of a portion of FIG. 1 depicting an alignment of a support member of the temperature control unit and support rails of the transportation cart.

A transportation cart 290 may be configured to receive frame 15 supporting container 10 holding the biopharmaceutical material to allow the biopharmaceutical material to be transported and/or stored therein as depicted in FIG. 7. For example, a width 230 of frame 15 may be less than or equal to a dimension or width 295 of a cart channel 297 of cart 290 to allow frame 15 to be received in cart 290.

In one example, each slot 25 of temperature control unit 20 may also include a support member 122 for holding frame 15 in slot 25 of interior 26 of temperature control unit 20, as depicted in FIGS. 1 and 7. Also, support 122 may include one or more frame support rails 121 and an opening 24 for receiving frame 15, as depicted in FIGS. 1, 2, 3 and 7. Specifically, a top portion 17 of frame 15 may be located on frame support rails 121 while flexible container 10 and the remainder of frame 15 may be received in opening 24 of support member 122 in slot 25. In an alternate embodiment, frame 15 may include projections (not shown) on an outside surface thereof which may be engaged with grooves (not shown) on an interior surface of frame support rails 121 to support frame 15 in slot 25. Further, the projections could be on support rails 121 and the grooves could be on frame 15. In another embodiment, frame 15 may rest on a bottom surface 291 of slot 25 with support rails 121 providing lateral support for frame 15.

Temperature control unit 20 and transportation cart 290 may be located adjacent one another such that frame 15 may be slid off support member 122 into channel 297 of transportation cart 290. Also, cart channel 297 may include one or more channel supports or support rails 292 for supporting frame 15 in cart channel 297. In one example, a height of a top of support member 122 (e.g., frame support rails 121) may be at a same height as a top of support rail 292 to facilitate movement therebetween. In a different example, a bottom of frame 15, when attached to support member 122, may be at a same height as a bottom 298 of cart channel 297 to facilitate movement of frame 15 from one to the other. Thus, frame 15 may be easily moved from interior 26 (e.g., from slot 25) of temperature control unit 20 to channel 297 of cart 290, when temperature control unit 20 and cart 290 are located adjacent to each other. For example, frame 15 may be manually slid onto rails 121 from transportation cart 297 located adjacent temperature control unit 20. Frame support rails 121 may be formed or coated with a material which allows frame 15 to be easily slid onto or off of such material. As depicted in FIGS. 1, 7 and 8, transportation cart 290 may have multiple channels 297 for receiving multiple frames 15 (not shown in FIG. 8) when located adjacent temperature control unit 20 having multiple slots 25. As is evident from FIG. 8, frame 15 may be slid from cart 290 directly into slots 25 by a user. Further, such frames may be slid from slots 25 into channel 297 in the same manner.

Temperature control unit 20 may also include one or more recesses 23 for receiving one or more alignment tabs 293, as depicted in FIGS. 1, 8 and 9. The alignment tabs are sized to fit into the recesses 23 so that by receiving alignment tab 293 in recesses 23, slot 25 may be aligned with channel 297. Such alignment facilitates the sliding of frame 15 from channel 297 of cart 290 into slot 25 of interior 26 of temperature control unit 20 or vice versa. More specifically, as depicted in FIG. 1, support rails 121 of support member 122 may be aligned with rails 292 such that frame 15 may be slid in a straight line from temperature control unit 20 to cart 290 or vice versa in response to aligning tabs 293 being received in recesses 23. Alternatively, in an example not shown, temperature control unit 20 could include aligning tabs (not shown) receivable in recesses (not shown) of cart 290. In a further example, temperature control unit 20 could include one or more recesses and one or more tabs while cart 290 may also include one or more recesses and one or more tabs with respective tabs being received in respective recesses to align the temperature control unit and cart.

In an example not depicted, cart 290 may have insulated walls (not shown) for reducing heat losses during storage or transportation of frame 15 holding one or more flexible containers 10. In addition, for long term storage of the biopharmaceutical product contained in flexible container 10, in either a liquid or a frozen state, a walk-in, a chest or a cabinet chiller or freezer (not shown) can be equipped with rails or channel supports or support rails (not shown) adapted to receive frames 15. Such rails or supports may also be at a same height relative to rails 292 to facilitate movement therebetween by a user.

In another example not depicted, temperature control unit 20 may be movable on wheels (not shown) thereby allowing it to be pulled or pushed along a track (not shown) by a pulling mechanism (not shown). This movement may include oscillation or reciprocation of temperature control unit 20. For example, temperature control unit 20 may move from a first position, travel along a track (not shown) to a second position, and it may then reverse course to return to the first position. The distance between these positions defines a stroke distance. The track may be configured to maintain the wheels (not shown) therebetween. Other examples of such movement include movement with varying acceleration, oscillatory movement with stops at the end of each stroke, and movement with superimposed vibrations, as described in co-owned U.S. patent application Ser. No. 09/579,846, which is hereby incorporated herein by reference. Also, the track (not shown) may be, for example, U-shaped, V-shaped, L-shaped, or inverted V-shaped to keep temperature control unit 20 moving in a fixed direction and/or a fixed route, as is also described in the referenced patent application.

Such movement of temperature control unit 20 having frame 15 and container 10 therein may cause agitation of, and thereby promote thawing and mixing of, biopharmaceutical materials held in container 10. Such mixing could be performed for the purpose of processing and could be combined therewith, such as: dissolution, homogenization, chemical/biochemical reactions, formulations, or compounding. For example, the force imposed by one or more of the sides of container 10 (e.g., first side 12) due to movement thereof may cause turbulence of portions or the whole volume of the biopharmaceutical material held in container 10. Such turbulence may promote thawing and mixing of the biopharmaceutical materials. More particularly, thawing rates of biopharmaceutical materials may be accelerated by generation of movement of partially-thawed solid-liquid mixture comprising a biopharmaceutical solution against walls of a container which may contact heat transfer surfaces, such as plates 28. This movement may be generated such that a liquid is moving against the walls and a solid in the liquid is moving against the liquid and against the walls. The patterns of liquid and solid movement may or may not be similar (the floating solid mass dynamics inside the vessel may or may not be similar to the liquid mass dynamics). Therefore, movement parameters, such as stroke and frequency, may change after the solid part is completely thawed. For example, during thawing of the biopharmaceutical material an oscillating or reciprocating rate of temperature control unit 20 may be greater than the rate after biopharmaceutical material has thawed and mixing without thawing is occurring. Such rates may be determined based on various factors, including liquid level, time and/or distance of oscillation, and geometry of the container being utilized.

The described dynamic movements of liquid and solid versus the container and its internal structures may turbulize the liquid phase, affect the boundary layer at the heat transfer surfaces, e.g., heated walls and bottom of the container, and at the melting solid surface, and mix the liquid. As a result, the heat transfer between the surfaces and liquid and solid phases of the biopharmaceutical solution is significantly enhanced. Increased heat transfer rate leads to very rapid thawing which may reduce or eliminate product degradation present in conventional, slow thawing, processes.

Also, the mixing described above depends on container shape, liquid depth, and motion parameters (e.g., frequency, amplitude). Further, such mixing is noninvasive since it is not necessary to insert an agitator or other mixer therein to facilitate such mixing. Instead, the mixing is caused by the forces imposed on the biopharmaceutical material in container 10 due to the motion of temperature control unit 20 which thereby causes turbulence of the biopharmaceutical materials. The noninvasive nature of this mixing inhibits contamination of the biopharmaceutical materials since no mixing mechanism needs to be inserted into container 10 and thus the contents thereof may be mixed without such container being opened. Sterility of the biopharmaceutical material may thus be maintained. Further, in another example, environmental contamination due to biohazardous materials, held in container 10 may be inhibited since there is no need to open container 10 to insert a mixing mechanism therein which could contaminate an ambient environment when removed from container 10.

As described above, movement, e.g., oscillation or reciprocation, of temperature control unit 20 may be utilized to promote thawing and mixing of biopharmaceutical material held in container 10. Such oscillatory motion may be harmonic or disharmonic. Further, such motion may be micromotion (i.e., small amplitude and high frequency) or macromotion (i.e., large amplitude and low frequency), as described in co-owned U.S. patent application Ser. No. 09/579,846. Further, a combination of micromotion and macromotion could be utilized. Such motion may accelerate thawing as compared to motionless thawing and enhance mixing and product homogenization. The frequency of the oscillation of the movement of temperature control unit 20 along the track (not shown) may preferably range up to 20 Hz when used for thawing. Such movement may also be superimposed with a higher frequency motion, such as a motion at 50 Hz, for example. Also, for mixing and other processing higher frequencies may be used in the movement along the track (not shown).

Another example of a temperature control unit 400 configured to receive flexible container 10 supported by frame 15 is depicted in FIGS. 10–13. Frame 15 may be received on a receiving frame 401 having a first rail 402 and a second rail 403 in a cavity or an interior 415 of temperature control unit 400. Heat transfer plates 428 are movable toward each other and may compress and control a temperature of biopharmaceutical material held in flexible container 10. Heat transfer fluids may be sent to and received from plates 428 by heat transfer conduits 410. Movement of plates 428 may be operatively caused by a linear actuator or piston 405 which may extend and contract as manually actuated or controlled by a computing unit (not shown). The contraction of piston 405 (depicted in phantom in FIG. 10) may cause movement of plates 428 toward each other while the extension of piston 405 (depicted in FIG. 10) may cause movement of plates 428 away from one another.

Specifically, the contraction of piston 405 may rotate a drive shaft 420 via a drive shaft member 406 to rotate a first pivoting member 425 to drive a first heat transfer plate 429 of heat transfer plates 428 toward flexible container 10 and a second heat transfer plate 427 of heat transfer plates 428. A second pivoting member 430 supports a bottom portion of first plate 429 and pivots on a pivotable shaft 432. An intermediate linking member 435 may be connected to shaft 420 whereby a rotation of shaft 420 due to a contraction of piston 405 causes movement of intermediate linking member 435. A cross linking member 440 may be coupled to intermediate linking member 435 via a pin 437 such that movement of intermediate linking member 435 due to rotation of shaft 420 may cause cross linking member 440 to move toward a right side 450 of temperature control unit 400. Cross-linking member 440 may also be connected to a second driven shaft 470 via a second driven shaft member 426. A third pivoting member 460 may be connected to second driven shaft 470 and second plate 427. Thus, movement of cross-linking member 440 toward right side 450 may cause movement of second driven shaft 470 causing rotation of third pivoting member 460 and thus second plate 427 toward flexible container 10 and first plate 429. A fourth pivoting member 465 may be connected to second plate 427 and may pivot about a pivotable shaft 467 to support a bottom portion of second plate 427. It will be understood by those skilled in the art that an extension of piston 405 may cause first plate 429 and second plate 427 to move away from one another and flexible container 10. Also, further pivoting members 480 may be connected to drive shaft 420, second driven shaft 70, pivoting shaft 432, and pivoting shaft 467 and plates 428 to support such plates and allow rotation thereof toward each other.

Also, frame 15 supporting flexible container 10 may be moved, reciprocated or oscillated within interior 415 of temperature control unit 400 to agitate the contents of container 10. More specifically, such agitation promotes thawing and mixing of biopharmaceutical materials held in flexible container 10, when frame 15 is received by receiving frame 401. For example, reciprocation of receiving frame 401 may be caused by a reciprocating piston 500 located outside interior 415 and mounted to an agitator mount 505 as shown in FIG. 11. Reciprocating piston 500 may be configured to extend and contract to reciprocate receiving frame 401 (FIG. 12) in interior 415. Receiving frame 401 may be movable in a direction of such extension and contraction on reciprocating pivoting members 510 which connect descending connecting members 520 of receiving frame 410 to projecting connecting members 530 connected to a lower platform 540, as depicted in FIGS. 11 and 12. Reciprocating pivoting members 510 are connected to descending connecting members 520 and projecting connecting members 530 via pins 550 at opposite ends of reciprocating pivoting members 510 to allow such movement. Interior 415 is sealed to inhibit leakage of biopharmaceutical materials or other materials outside of interior 415. Thus, reciprocating pivoting members 510, descending connecting members 520, and projecting connecting members 530 may be protected from spillage of product which might inhibit the agitation of the biopharmaceutical material caused by the movement of flexible container 10 supported by frame 15 in receiving frame 401. Interior 415 may also include a removable pan 551 to collect any spillage of biopharmaceutical materials or other materials which may occur inside interior 415. Alternatively, pan 551 may not be removable and it may include a valve to allow selective release of materials collected therein.

Also, it will be understood by those skilled in the art that the movement (e.g., reciprocation) of receiving frame 401 in interior 415 may be caused by any means for moving receiving frame 401. For example, such movement may be caused mechanically, such as by an electric motor with a gear box and a cam with an arm. Other examples include an electromagnetic solenoid, a hydraulic or pneumatic piston, and return by a spring. Further examples include electromechanical devices such as a crank shaft coupled to a motor or other electromechanical means. Additionally, it is evident from FIGS. 10–13 that temperature control unit 400 may be moved and/or reciprocated on wheels 560. Moreover, receiving frame 401 may be stationary relative to cavity 415 or receiving frame 401 may be moved within interior 415 simultaneously to temperature control unit 400 as a whole being moved on wheels 560. Such movement of receiving frame 401 may occur in a same direction or a different direction from temperature control unit 400 on wheels 560. Further, temperature control unit 400 may be moved by any means for causing movement, as described for receiving frame 401 and temperature control unit 20. In another unillustrated example, an interior or cavity of a temperature control unit may be moveable with a support or frame supporting a flexible container therein without the temperature control unit as a whole being moved.

Figure 14:
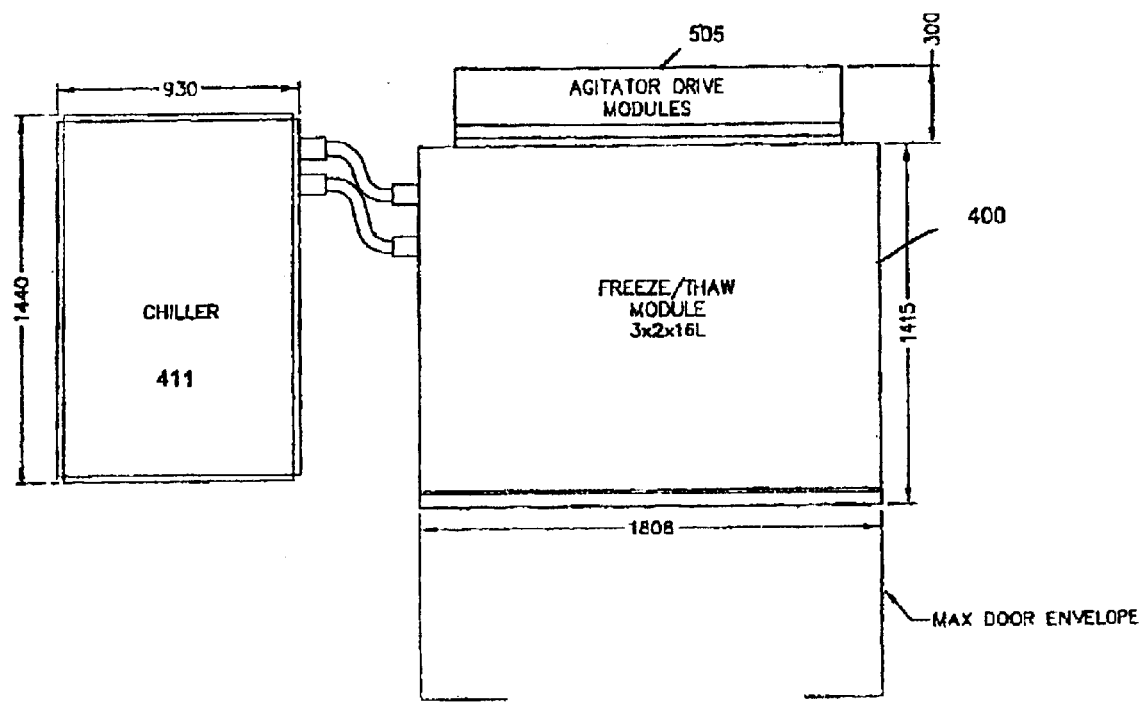
FIG. 14 is a top elevational view of the temperature control unit of FIG. 10 coupled to a chiller.
Figure 15:
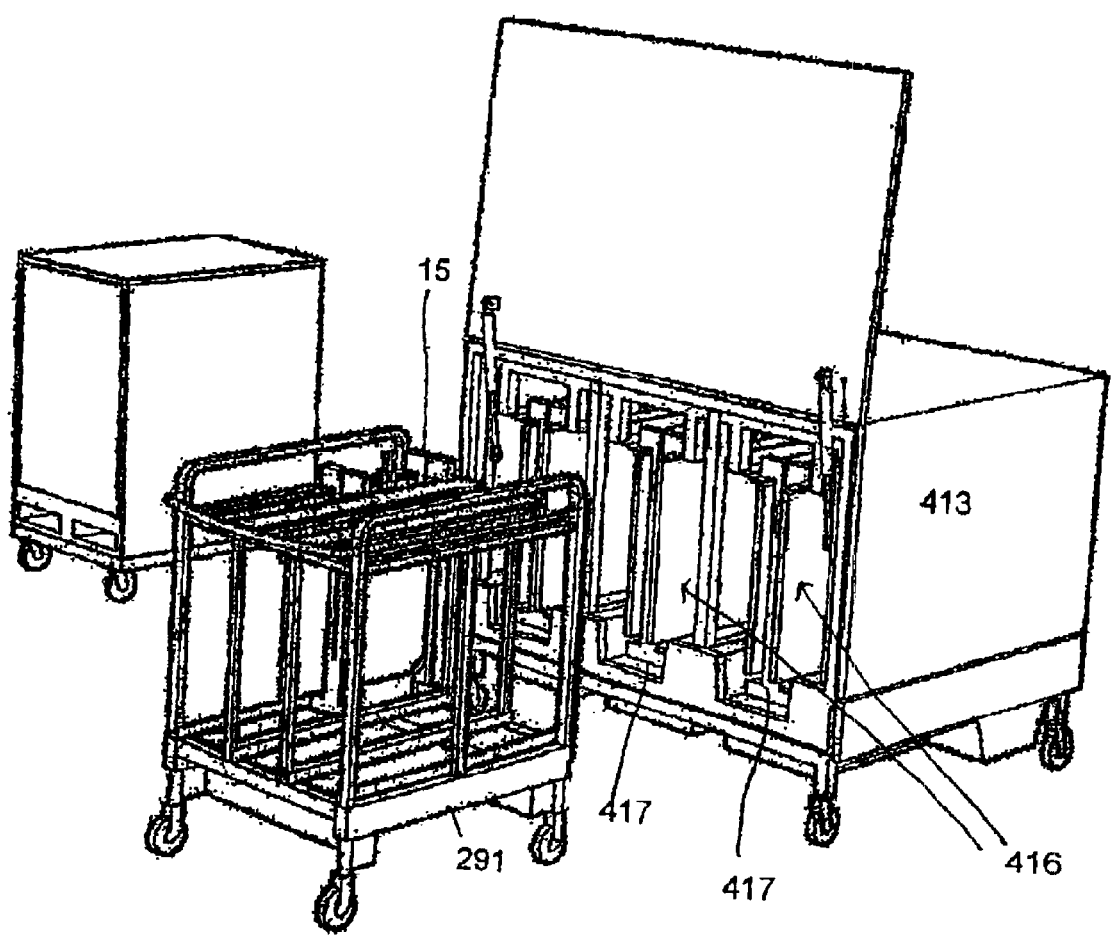
FIG. 15 is another embodiment of a temperature control unit having multiple interiors for receiving multiple flexible containers supported by multiple frames adjacent a cart having multiple channels to receive multiple frames.
Figure 16:
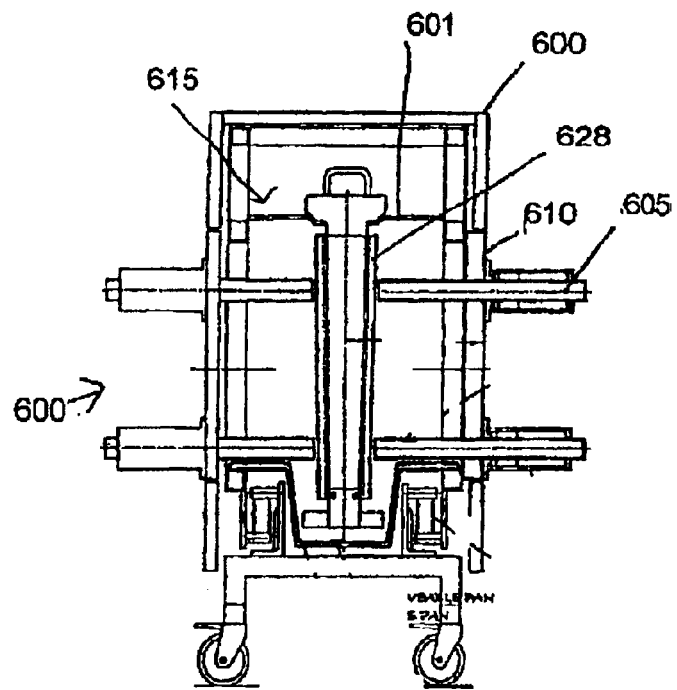
FIG. 16 is a side cross-sectional view of another embodiment of a temperature control unit in accordance with the present invention.
Figure 17:
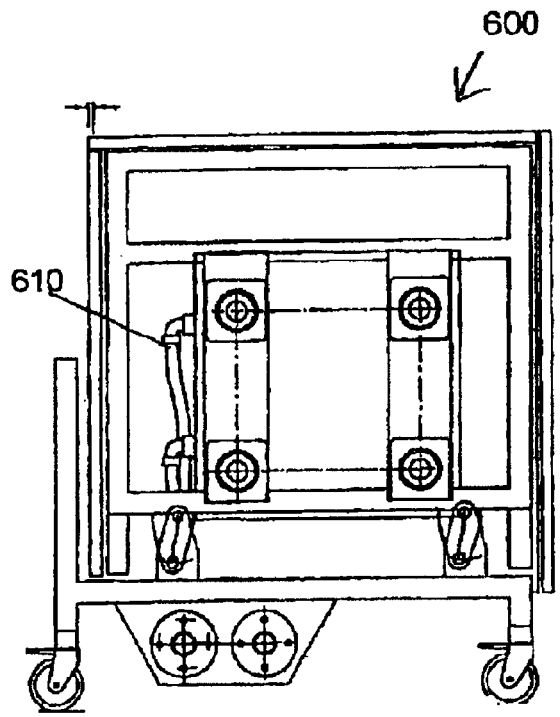
FIG. 17 is a front cross-sectional view of the temperature control unit of FIG. 16.
Figure 18:
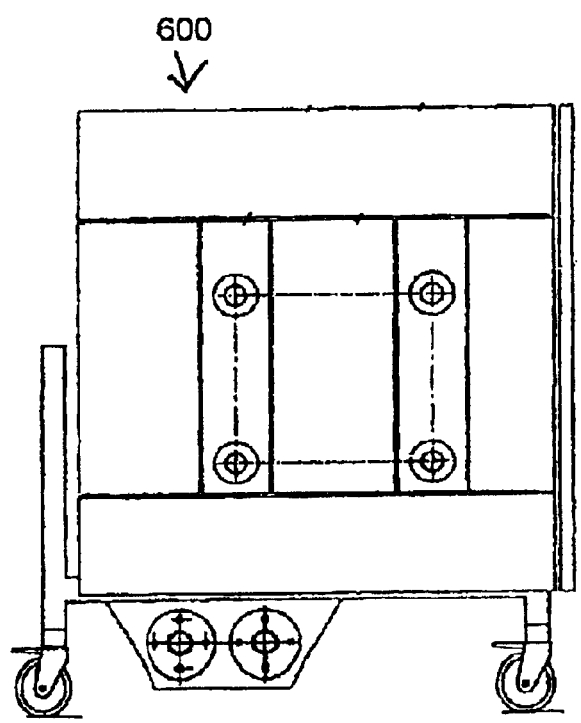
FIG. 18 is a rear cross-sectional view of the temperature control unit of FIG. 16.
Figure 19:
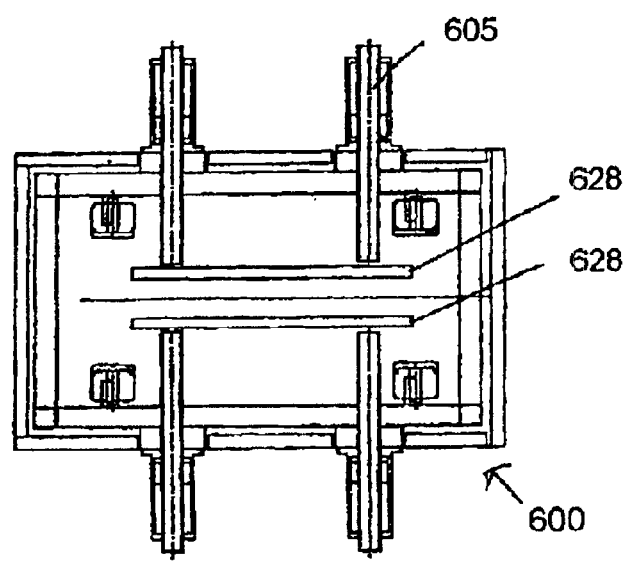
FIG. 19 is a top cross-sectional view of the temperature control unit of FIG. 16.
Figure 21:
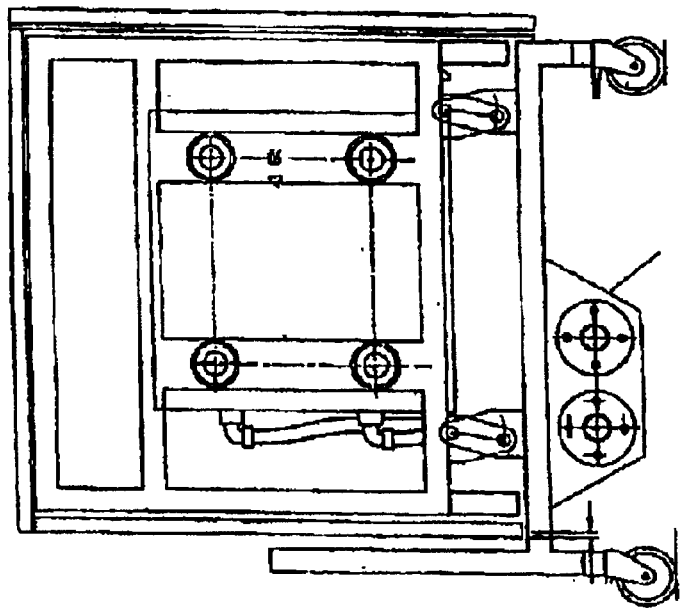
FIG. 21 is a front cross-sectional view of the temperature control unit of FIG. 20.
Figure 20:
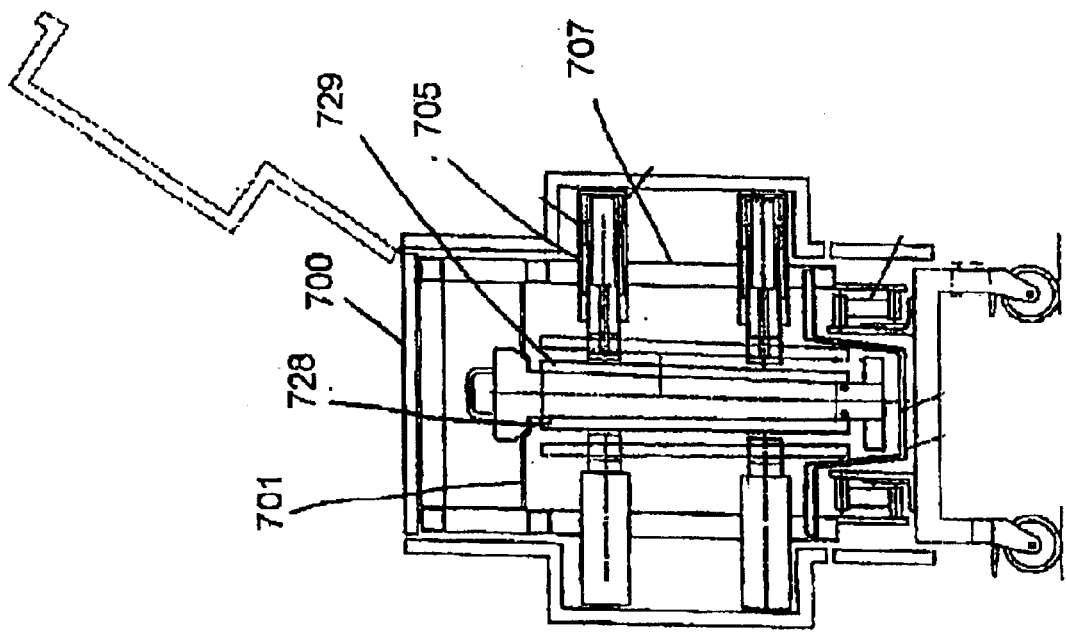
FIG. 20 is a side cross-sectional view of another embodiment of a temperature control unit in accordance with the present invention.
Figure 22:
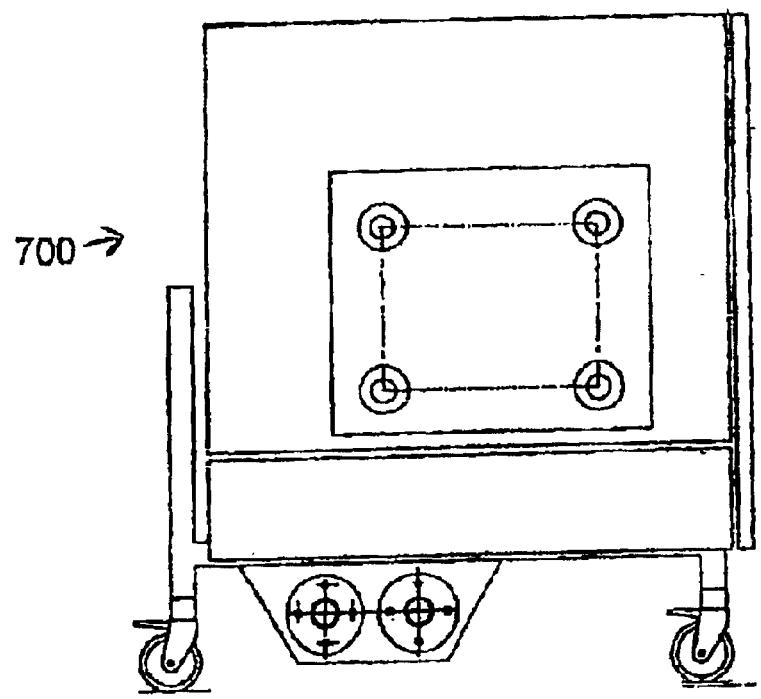
FIG. 22 is a rear cross-sectional view of the temperature control until of FIG. 20.
Figure 23:
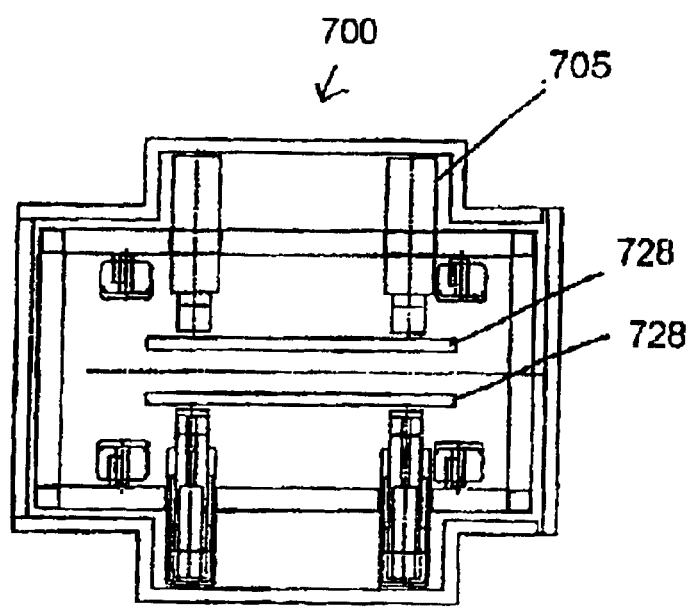
FIG. 23 is a top cross-sectional view of the temperature control unit of FIG. 20.

FIG. 14 depicts temperature control unit 400 coupled to a temperature regulator or chiller 411 configured to provide heat transfer fluid to plates 428 (FIGS. 10–13) to control the temperature of biopharmaceutical material held in flexible container 10 in interior 415 (FIGS. 10–13). Further, FIG. 15 depicts a temperature control unit 413 identical to temperature control unit 400 except that it includes an interior 416 having multiple slots 417 for receiving multiple frames 15 holding multiple flexible containers 10. Each of slots 417 may include plates 428 coupled to temperature regulator and/or chiller 411 to control the temperature of biopharmaceutical material held therein. The temperature of the biopharmaceutical material may be controlled and/or monitored by temperature sensors and/or controllers located within the temperature control unit, as previously described herein, thermally coupled to the chiller. Temperatures determined by the sensors and/or controllers may be processed by a computing unit to control the temperature of the heat transfer fluid provided by the chiller to the temperature control unit. Further, each of slots 417 may be moveable on multiple receiving frames 401 to allow the agitation of biopharmaceutical material held in flexible container 10 held in each of slots 417. Transportation cart 290 may be located adjacent temperature control unit 413 for transferring frame 15 into one or more of slots 417.

A further example of a temperature control unit 600 configured to receive flexible container 10 supported by frame 15 is depicted in FIGS. 16–19. Frame 15 may be received on a receiving frame 601 in an interior 615 of temperature control unit 600. Heat transfer plates 628 are movable toward and may compress and control a temperature of biopharmaceutical material held in flexible container 10. Heat transfer fluids may be sent to and received from plates 628 by heat transfer conduits 610. Movement of plates 628 may be operatively caused by linear actuators or pistons 605 which may extend and contract as manually actuated or controlled by a computing unit (not shown). The extension of pistons 605, as depicted in FIGS. 16–19 may cause movement of plates 628 toward each other while the contraction of pistons 605 may cause movement of plates 628 away from one another. Thus, pistons 605 may be extended toward flexible container 10 when it is desired to compress and/or freeze the biopharmaceutical material held in flexible container 10. Accordingly, pistons 605 may be contracted to allow frame 15 to be inserted on receiving frame 601 or removed therefrom. Pistons 605 are mounted on an outer surface 610 of temperature control unit 600. In another example, depicted in FIGS. 20–23, pistons 705 are mounted on an interior frame 707 of a temperature control unit 700 and may cause movement of plates 728 toward one another to promote freezing and/or compressing of biopharmaceutical materials held in flexible container 10 supported by frame 15 on a receiving frame 701. Thus, it will be understood by those skilled in the art that heat transfer plates (e.g., plates 28, plates 428, plates 628, and plates 728) may be moved toward or away from each other using various means.

Figure 24:
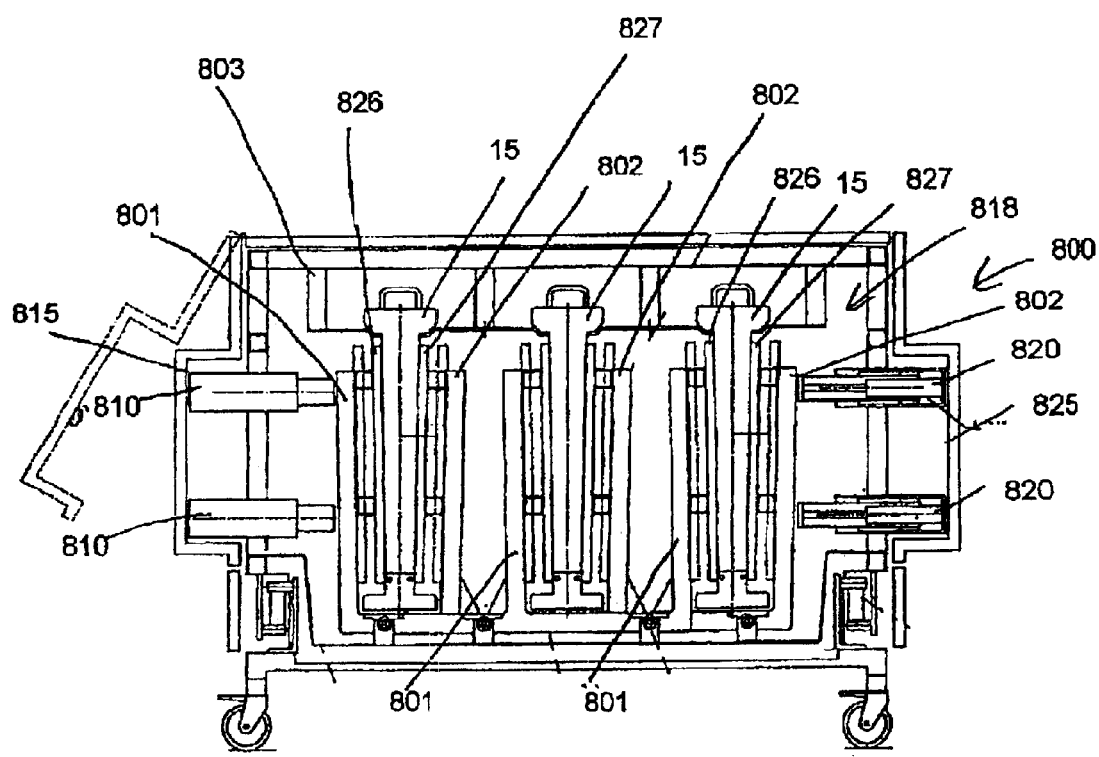
FIG. 24 is a front cross-sectional view of another embodiment of the temperature control unit in accordance with the present invention.

An example of a temperature control unit 800 configured to receive multiple frames 15 is depicted in FIG. 24, and includes a left plate support frame 801 and a right plate support frame 802. Left plate support frame 801 is connected to left heat transfer plates 826 and right plate support frame 802 is connected to right heat transfer plates 827. Frames 15 are received on a support frame 803. Left linear actuators or pistons 810 are mounted to a side wall 815 of temperature control unit 800. Pistons 810 may extend to force left plates 826 toward right plates 827 by applying force to extend left plate support frame 801 or pistons 810 may contract to move left plates 826 away from right plates 827 by retracting left plate support frame 801. Right pistons 820 may be mounted to a right wall 825 of temperature control unit 800. Right plates 827 may be moved toward left plates 826 by an extension of pistons 820 applying a force to right plate support frame 802. Right plates 827 may be moved away from left plates 826 by a contraction of pistons 820. As described above, biopharmaceutical materials held in flexible container 10 supported by a frame 15 may be frozen or have its temperature otherwise controlled when flexible container 10 is contacted and/or compressed by plates (e.g., plates 826 and 827) being moved toward each other. Further, left plates 826 and right plates 827 may be moved away from one another to facilitate insertion of frame 15 supporting flexible container 10 into temperature control unit 800.

Also, it will be understood by one skilled in the art that various frames might be utilized to support flexible container 10 and to be received in a temperature control unit (e.g. temperature control unit 20, temperature control unit 400, temperature control unit 600, and temperature control unit 700) along with being engageable with support member 122 or other means for support (e.g. support rails 121, receiving frame 401, receiving frame 601, receiving frame 701, and receiving frame 803). Examples of such frames are described in co-owned U.S. patent application Ser. No. 10/254,036 filed on Sep. 23, 2002 and titled "Systems and Method for Freezing and Storing Biopharmaceutical Material.

Although the containers are described herein as flexible containers, the containers may be made of a semi-rigid material such as polyethylene or the like. Such a semi-rigid material may retain its shape and/or stand up by itself when empty and when filled with a biopharmaceutical material. An example of such a container could include a container similar to a standard plastic milk jug. Containers made of such similar semi-rigid materials may benefit from additional rigidity supplied by attachment to a frame, for example. Further, the containers whether formed of a flexible or semi-rigid material, contain outer surfaces which contact the interior surfaces (e.g., heat transfer plates) of a temperature control unit (e.g., temperature control unit 20) so that there is direct contact between the cooled (e.g., to a subzero temperature) or heated interior surfaces of the temperature control unit and the outer surfaces of the container containing biopharmaceutical materials. Alternatively, the outer surfaces of the containers for holding the biopharmaceutical materials may be in contact with air flow in an interior (e.g., interior 25) of the temperature control unit to cause the cooling and/or heating of the containers having the biopharmaceutical materials therein to cause the temperature of the biopharmaceutical materials to be controlled.

The biopharmaceutical material in the flexible containers described above may thus be cooled or otherwise thermoregulated in temperature control unit 20 (e.g., to a subzero temperature) or the other described temperature control units. When such operation is completed, the flexible containers may be removed from temperature control unit 20 by removing the flexible containers and the frames, or other support structures which the flexible containers are received in or connected to, for example. The frames or other support structures holding the flexible containers may be stored in a large chiller or freezer with an interior air temperature of about negative 20 degrees Celsius, for example.

A typical process for processing and/or preserving a biopharmaceutical material is described as follows. Flexible container 10 is inserted into frame 15, as depicted in FIGS. 5–6. Also, frame 15 may be placed in transportation cart 290 (FIG. 1) and transported to a filling station (not shown). Biopharmaceutical material, for example liquid biopharmaceutical material, is inserted through conduit 120 into flexible container 10. In one example, frame 15 may be slid from transportation cart 290 to scale supporting rails (not shown) of a scale (not shown). Flexible container 10 may then be filled to a certain weight determined by the scale. In another example, cart 290 may be moved onto a scale (not shown), which does not include scale rails and which is configured to receive cart 290, and flexible container 10 may be filled thereon.

After filling, flexible container 10, while held in frame 15, may be transferred from transportation cart 290 into temperature control unit 20, as shown in FIG. 1, where plates 28 may compress container 10 and the biopharmaceutical material therein. More specifically, frame 15 may be slid from support rails 292 of cart channel 297 onto support member 122 of slot 25. The biopharmaceutical contents are frozen in temperature control unit 20 in a controlled manner (e.g., to negative 20 degrees Celsius or below), for example, such that the freeze rate (including the dendritic freeze front velocity from the sides of the container to the center) is controlled within upper and lower limits, as described in U.S. patent application Ser. No. 09/905,488. Thus, cryoconcentration of the biopharmaceutical material is prevented or inhibited, thereby preventing undesirable degradation of the biopharmaceutical material. After the biopharmaceutical material in flexible container 10 is frozen, frame 15 and flexible container 10 may be removed from support member 122 of temperature control unit 20 and placed on support rails 292 of cart 290 for transport to a large freezer, for example, a walk-in freezer having an interior air temperature of about negative 20 degrees Celsius for storage, as is typically present in large medical institutions (e.g., hospitals). Alternatively, container 10 may be moved from support rails 290 to freezer rails (not shown) in such a freezer.

Further, the above described flexible containers may be removed from a freezer or other system for storage of the flexible containers and contents thereof at a controlled temperature. These flexible containers having biopharmaceutical material therein may then be received in a temperature control unit for heating, melting, agitating, mixing and/or thawing the biopharmaceutical material contained in the flexible containers. For example, frame 15 supporting flexible container 10 having frozen biopharmaceutical material therein may be placed in temperature control unit 20 where its temperature may be controlled (e.g. thawed) by heat transfer plate(s) 28. Further, temperature control unit 20 might be moved, e.g. reciprocated, along a track (not shown) to agitate the biopharmaceutical material to facilitate thawing and/or mixing thereof. Also, frame 15 supporting flexible container 10 may be moved or reciprocated in slot 25 of temperature control unit 20 to further facilitate such thawing. Upon completion of a thawing process, the biopharmaceutical material in flexible container 10 may be mixed by moving temperature control unit 20 along a track (not shown) and/or moving frame 15 in slot 25 of temperature control unit 20. In another example, liquid biopharmaceutical material may be agitated by movement of flexible container 10 held in frame 20 in an interior of a temperature control unit during a freezing process until a point prior to formation of ice crystals in the biopharmaceutical material. Such agitation will be terminated prior to such formation and the freezing process will continue with the frame in a stationary position. The described methods are also applicable to temperature control unit 400, temperature control unit 600, and temperature control unit 700, as will be understood by those skilled in the art.

From the above description, it will be understood to one skilled in the art that the flexible containers described herein may be adapted for use in containers, frames, storage units, support structures, transportation devices, temperature control units, heat exchangers, vessels, and/or processors of various shapes or sizes. Further, the frames, containers, support structures, heat exchangers, temperature control units, and/or processors may be adapted to receive flexible containers of various shapes or sizes. These frames or support structures may be configured for long or short term storage of the flexible containers containing biopharmaceutical materials in liquid or frozen state, or may be adapted to transport the flexible containers containing biopharmaceutical materials in liquid or frozen state. For example, the temperature control unit may be insulated to allow the material to remain at a given temperature for a prolonged period of time. Furthermore, these flexible containers, frames, containers, support structures, temperature control units, heat exchangers, and/or processors may be adapted for utilization with materials other than biopharmaceutical materials. Finally, the storage containers, support structures, temperature control units, or frames may be equipped with various transport mechanisms, such as wheels, glides, sliders, dry-ice storage compartments or other devices to facilitate transport and organization thereof.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A system for freezing a biopharmaceutical material, said system comprising:
    a cavity configured for receiving a frame configured to receive a biopharmaceutical material holding container therein;
    at least a pair of opposed surfaces facing the biopharmaceutical material holding container;
    at least one of said opposed surfaces comprising a movable contacting surface configured to contact the container to inhibit a clearance between the container and said movable contacting surface;
    at least one heat transfer surface, said at least one heat transfer surface being thermally coupled to said biopharmaceutical holding container in response to said movable contacting surface contacting said container; and
    a support member configured to support the frame in said cavity to allow said movable contacting surface to contact the container when the container is received in the frame and the frame is received in the cavity.

2. The system of claim 1 wherein said contacting surface is configured to compress said container to inhibit a clearance between the container and said at least one heat transfer surface.

3. The system of claim 1 wherein said at least one heat transfer surface comprises at least one of said opposed surfaces.

4. The system of claim 1 wherein the container comprises at least one of a flexible container and a semi-rigid container.

5. The system of claim 1 wherein the frame is configured for at least one of protecting and supporting the container.

6. The system of claim 5 wherein the frame comprises a first side having a first opening and a second side having a second opening, wherein the container is in communication with said cavity through the first opening and the second opening, when the container is received in the frame and the frame is received in said cavity.

7. The system of claim 6 wherein said at least one heat transfer surface is configured to contact the container through at least one of the first opening and the second opening of the frame.

8. The system of claim 5 wherein the frame comprises a thickness and said cavity comprises a slot, said slot being dimensioned to receive the frame therein.

9. The system of claim 8 wherein the frame comprises a first frame and said slot is configured to receive a second frame therein.

10. The system of claim 8 wherein said support member is configured to support the frame in said slot.

11. The system of claim 1 wherein the frame comprises a first frame and said support member is configured to support a second frame.

12. The system of claim 8 wherein said slot comprises a first slot for receiving the frame and further comprising a second slot for receiving a second frame.

13. The system of claim 5 further comprising at least one driver for moving the frame within said cavity to cause mixing of the biopharmaceutical material during a thawing cycle.

14. The system of claim 5 further comprising at least one driver for moving the frame within said cavity to cause mixing of the biopharmaceutical material during a freezing cycle prior to a formation of ice crystals.

15. The system of claim 5 further comprising at least one driver for moving the frame within said cavity to agitate the biopharmaceutical material.

16. The system of claim 5 further comprising at least one driver for moving said cavity having the frame received therein to cause mixing of the biopharmaceutical material during a thawing cycle.

17. The system of claim 5 further comprising at least one driver for moving said cavity having the frame received therein to cause mixing of the biopharmaceutical material during a freezing cycle prior to a formation of ice crystals.

18. The system of claim 5 further comprising at least one driver for moving said cavity having the frame received therein to agitate the biopharmaceutical material.

19. The system of claim 1 further comprising means for regulating a temperature of the biopharmaceutical material when the biopharmaceutical material is contained in the container in said cavity.

20. The system of claim 1 further comprising a controller for regulating at least one of a flow of a heat transfer fluid to said at least one heat transfer surface and a temperature of the heat transfer fluid.

21. A method for freezing a biopharmaceutical material, the method comprising:
    inserting a biopharmaceutical material holding container into a cavity of a temperature control unit;
    moving at least one contacting surface in the cavity to contact the container to inhibit a clearance between the container and the at least one contacting surface;
    thermally coupling the biopharmaceutical material holding container to at least one heat transfer surface in response to the at least one contacting surface contacting the container inserting a frame supporting the container into the cavity, inserting the frame onto a support member in the cavity, and inserting a second frame supporting a second container on the support member.

22. The method of claim 21 wherein the contacting comprises compressing the container to inhibit a clearance between the container and the at least one heat transfer surface.

23. The method of claim 21 wherein the at least one contacting surface comprises the at least one heat transfer surface.

24. The method of claim 21 wherein the contacting comprises contacting the container through at least one opening in a frame supporting the container.

25. The method of claim 21 wherein the container comprises at least one of a flexible container and a semi-rigid container.

26. The method of claim 21 further comprising regulating a temperature of the cavity to regulate a temperature of the biopharmaceutical material when the biopharmaceutical material is contained in the container in the cavity.

27. The method of claim 21 further comprising regulating a temperature of the at least one heat transfer surface in the cavity to regulate a temperature of the biopharmaceutical material, when the biopharmaceutical material is contained in the container in the cavity.

28. The method of claim 21 wherein the support member is in a slot of the cavity.

* * * * *

UNITED STATES PATENT AND TRADEMARK OFFICE
CERTIFICATE OF CORRECTION

PATENT NO. : 6,945,056 B2
DATED : September 20, 2005
INVENTOR(S) : Brown et al.

It is certified that error appears in the above-identified patent and that said Letters Patent is hereby corrected as shown below:

Column 19,
Line 26, after the word "surface;" insert a new paragraph with the words -- inserting a frame supporting the container into the cavity, inserting the frame onto a support member in the cavity; and --.

Column 19, line 30 through Column 20, line 4,
Delete the words "inserting a frame supporting the container into the cavity, inserting the frame onto a support member in the cavity, and inserting a second frame supporting a second container on the support member." and insert -- ; and -- after the word "container".

Column 20,
Lines 1-2, insert a new paragraph with the words -- inserting a second frame supporting a second container on the support member. --.

Signed and Sealed this

Twentieth Day of December, 2005

JON W. DUDAS
*Director of the United States Patent and Trademark Office*